United States Patent [19]
Peyser et al.

[11] Patent Number: 5,700,270
[45] Date of Patent: Dec. 23, 1997

[54] SURGICAL CLIP APPLIER

[75] Inventors: Mark S. Peyser, Easton; Douglas J. Cuny, Bethel; Douglas W. Strauss, Hamden; Scott W. Reed, Shelton; Csaba L. Rethy, Fairfield; Ernie Aranyi, Easton, all of Conn.

[73] Assignee: United States Surgical Corporation, Norwalk, Conn.

[21] Appl. No.: 546,484

[22] Filed: Oct. 20, 1995

[51] Int. Cl.$^6$ .................................................. A61B 17/10
[52] U.S. Cl. ............................................ 606/142; 606/143
[58] Field of Search ................................. 606/142, 143, 606/158, 157, 219

[56] References Cited

U.S. PATENT DOCUMENTS

| | | |
|---|---|---|
| 2,968,041 | 1/1961 | Skold . |
| 3,152,336 | 10/1964 | Brady . |
| 3,646,801 | 3/1972 | Carroll . |
| 3,753,438 | 8/1973 | Wood et al. . |
| 4,086,926 | 5/1978 | Green et al. . |
| 4,152,920 | 5/1979 | Green . |
| 4,166,466 | 9/1979 | Jarvik . |
| 4,185,762 | 1/1980 | Froehlich . |
| 4,196,836 | 4/1980 | Becht . |
| 4,201,314 | 5/1980 | Samuels et al. . |
| 4,226,242 | 10/1980 | Jarvik . |
| 4,228,895 | 10/1980 | Larkin . |
| 4,242,902 | 1/1981 | Green . |
| 4,246,903 | 1/1981 | Larkin . |
| 4,256,251 | 3/1981 | Moshofsky . |
| 4,296,751 | 10/1981 | Blake, III et al. . |
| 4,299,224 | 11/1981 | Noiles . |

(List continued on next page.)

FOREIGN PATENT DOCUMENTS

| | | |
|---|---|---|
| 0068046 | 1/1983 | European Pat. Off. . |
| 0406724 | 1/1991 | European Pat. Off. . |
| 0409569 | 1/1991 | European Pat. Off. . |
| 0507537 | 10/1992 | European Pat. Off. . |
| 0612505 | 8/1994 | European Pat. Off. . |
| 0623316 | 11/1994 | European Pat. Off. . |
| 8202825 | 9/1982 | WIPO . |
| 8801486 | 3/1988 | WIPO . |
| 9003763 | 4/1990 | WIPO . |
| 9421181 | 9/1994 | WIPO . |

OTHER PUBLICATIONS

Ethicon, "Ligaclip: Ligating Clips & Appliers", 1982.
Reynolds, Jr., "Metal Clip Techniques Utilizing Pistol Grip Appliers", *American Journal of Surgery*, vol. 143, Feb. 1982.
U.S. Surgical Corporation, Information Booklet for Auto Suture® Premium Surgiclip™ Titanium Disposable Automatic Clip Appliers.
Weck, "We've Corrected Everybody's Flaws. Even Our Own.", *Surgery: Gynecology & Obstetrics*, vol. 163, No. 3, Sep. 1986.
Weck, "Deep Surgery Advantage: Dramatic New Access Plus Automatic-Feed In Vessel Ligation".

*Primary Examiner*—Michael Buiz
*Assistant Examiner*—Daphja Shai

[57] ABSTRACT

A surgical clip applier includes a housing, a pair of handles pivotably connected to opposite sides of the housing, a channel assembly which is anchored to the housing and a jaw assembly which is anchored to the channel assembly. The jaws are opened and closed by a cam plate which is slidably positioned in the channel assembly and is provided with cam slots at its distal end to engage drive rivets positioned on the jaw members. A pusher bar assembly is also provided to feed clips from a series of clips to the jaw mechanism, and the instrument operates such that all moving components move in the same direction during the closing stroke of the handle, and then move in the same direction opposite to the closing direction when the handles are in the opening stroke. A novel lockout mechanism is also provided to render the instrument inoperable after all the clips have been utilized from the instrument.

21 Claims, 29 Drawing Sheets

U.S. PATENT DOCUMENTS

| | | |
|---|---|---|
| 4,316,468 | 2/1982 | Klieman et al. . |
| 4,325,376 | 4/1982 | Klieman et al. . |
| 4,372,316 | 2/1983 | Blake, III et al. . |
| 4,408,603 | 10/1983 | Blake, III et al. . |
| 4,410,125 | 10/1983 | Noiles et al. . |
| 4,412,539 | 11/1983 | Jarvik . |
| 4,425,915 | 1/1984 | Ivanov . |
| 4,427,008 | 1/1984 | Transue . |
| 4,430,997 | 2/1984 | DiGiovanni et al. . |
| 4,448,193 | 5/1984 | Ivanov . |
| 4,450,839 | 5/1984 | Transue . |
| 4,450,840 | 5/1984 | Mericle et al. . |
| 4,452,357 | 6/1984 | Klieman et al. . |
| 4,452,376 | 6/1984 | Klieman et al. . |
| 4,471,780 | 9/1984 | Menges et al. . |
| 4,478,218 | 10/1984 | Mericle . |
| 4,478,220 | 10/1984 | DiGiovanni et al. . |
| 4,480,640 | 11/1984 | Becht . |
| 4,480,641 | 11/1984 | Failla et al. . |
| 4,492,232 | 1/1985 | Green . |
| 4,500,024 | 2/1985 | DiGiovanni et al. . |
| 4,509,518 | 4/1985 | McGarry et al. . |
| 4,512,345 | 4/1985 | Green . |
| 4,522,207 | 6/1985 | Klieman et al. . |
| 4,532,925 | 8/1985 | Blake, III . |
| 4,534,351 | 8/1985 | Rothfuss et al. . |
| 4,549,544 | 10/1985 | Favaron . |
| 4,556,058 | 12/1985 | Green . |
| 4,557,263 | 12/1985 | Green . |
| 4,562,839 | 1/1986 | Blake, III et al. . |
| 4,565,199 | 1/1986 | Becht . |
| 4,572,183 | 2/1986 | Juska . |
| 4,576,166 | 3/1986 | Montgomery et al. . |
| 4,598,711 | 7/1986 | Deniega . |
| 4,611,595 | 9/1986 | Klieman et al. . |
| 4,616,650 | 10/1986 | Green et al. . |
| 4,624,254 | 11/1986 | McGarry et al. . |
| 4,637,395 | 1/1987 | Casper et al. . |
| 4,646,740 | 3/1987 | Peters et al. . |
| 4,662,373 | 5/1987 | Montgomery et al. . |
| 4,662,374 | 5/1987 | Blake, III . |
| 4,674,504 | 6/1987 | Klieman et al. . |
| 4,691,853 | 9/1987 | Storace . |
| 4,712,549 | 12/1987 | Peters et al. . |
| 4,850,355 | 7/1989 | Brooks et al. . |
| 4,967,949 | 11/1990 | Sandhaus . |
| 5,030,226 | 7/1991 | Green et al. ............................ 606/158 |
| 5,047,038 | 9/1991 | Peters et al. . |
| 5,049,152 | 9/1991 | Simon et al. . |
| 5,067,958 | 11/1991 | Sandhaus . |
| 5,084,057 | 1/1992 | Green et al. ............................ 606/142 |
| 5,100,420 | 3/1992 | Green et al. . |
| 5,104,395 | 4/1992 | Thornton et al. ........................ 606/143 |
| 5,112,343 | 5/1992 | Thornton . |
| 5,156,609 | 10/1992 | Nakao et al. . |
| 5,171,247 | 12/1992 | Hughett et al. ............................ 606/142 |
| 5,171,249 | 12/1992 | Stefanchik et al. . |
| 5,192,288 | 3/1993 | Thompson et al. . |
| 5,207,692 | 5/1993 | Kraus et al. . |
| 5,211,649 | 5/1993 | Kohler et al. . |
| 5,246,450 | 9/1993 | Thornton et al. . |
| 5,330,487 | 7/1994 | Thornton et al. . |
| 5,403,327 | 4/1995 | Thornton et al. . |
| 5,409,498 | 4/1995 | Braddock et al. . |
| 5,431,668 | 7/1995 | Burbank, III et al. . |

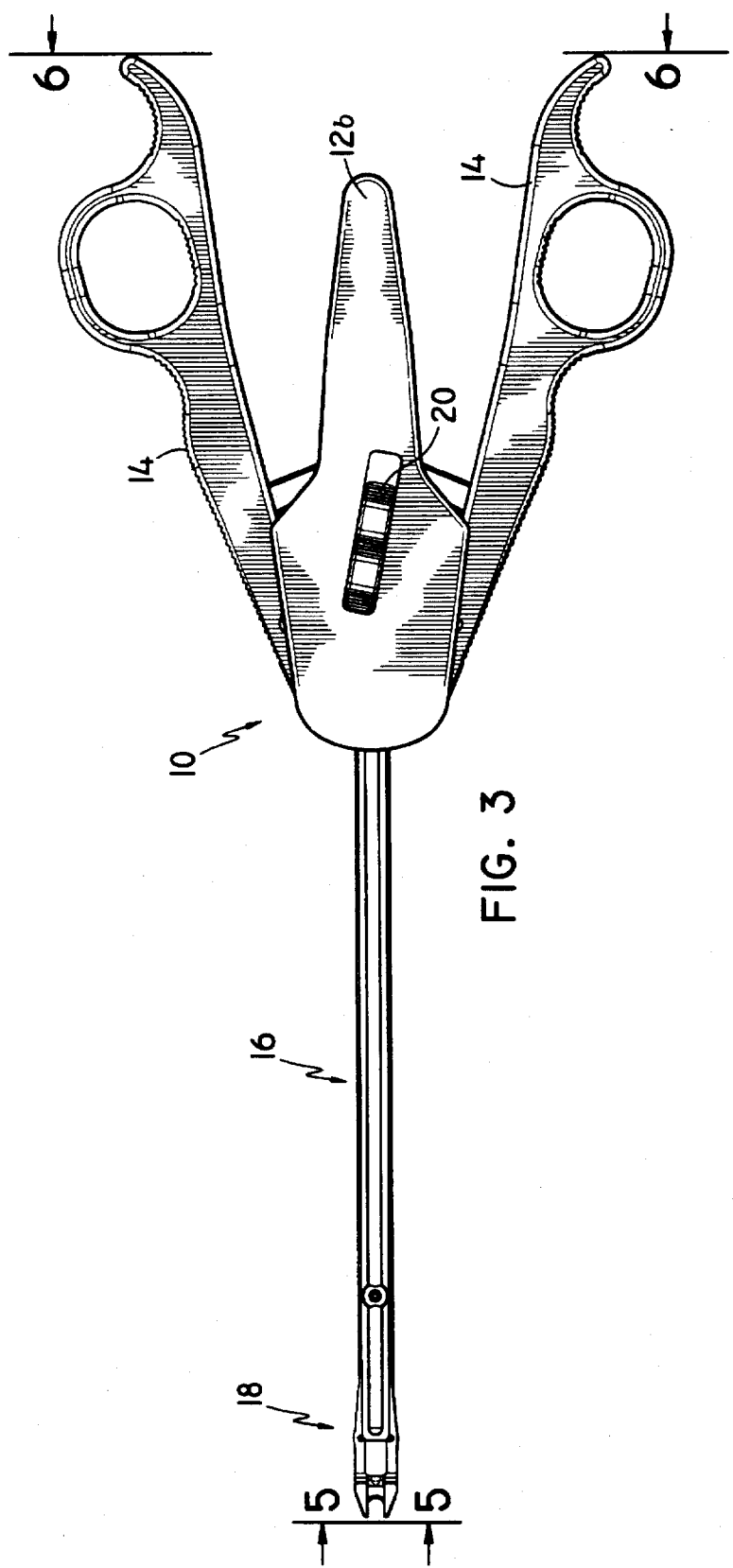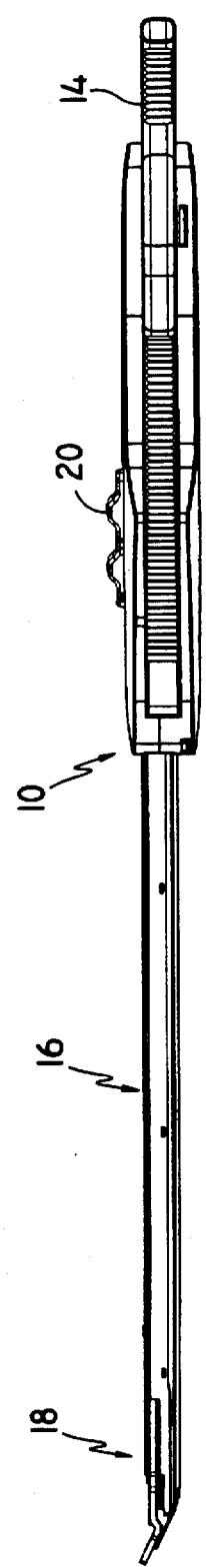
FIG. 3
FIG. 4

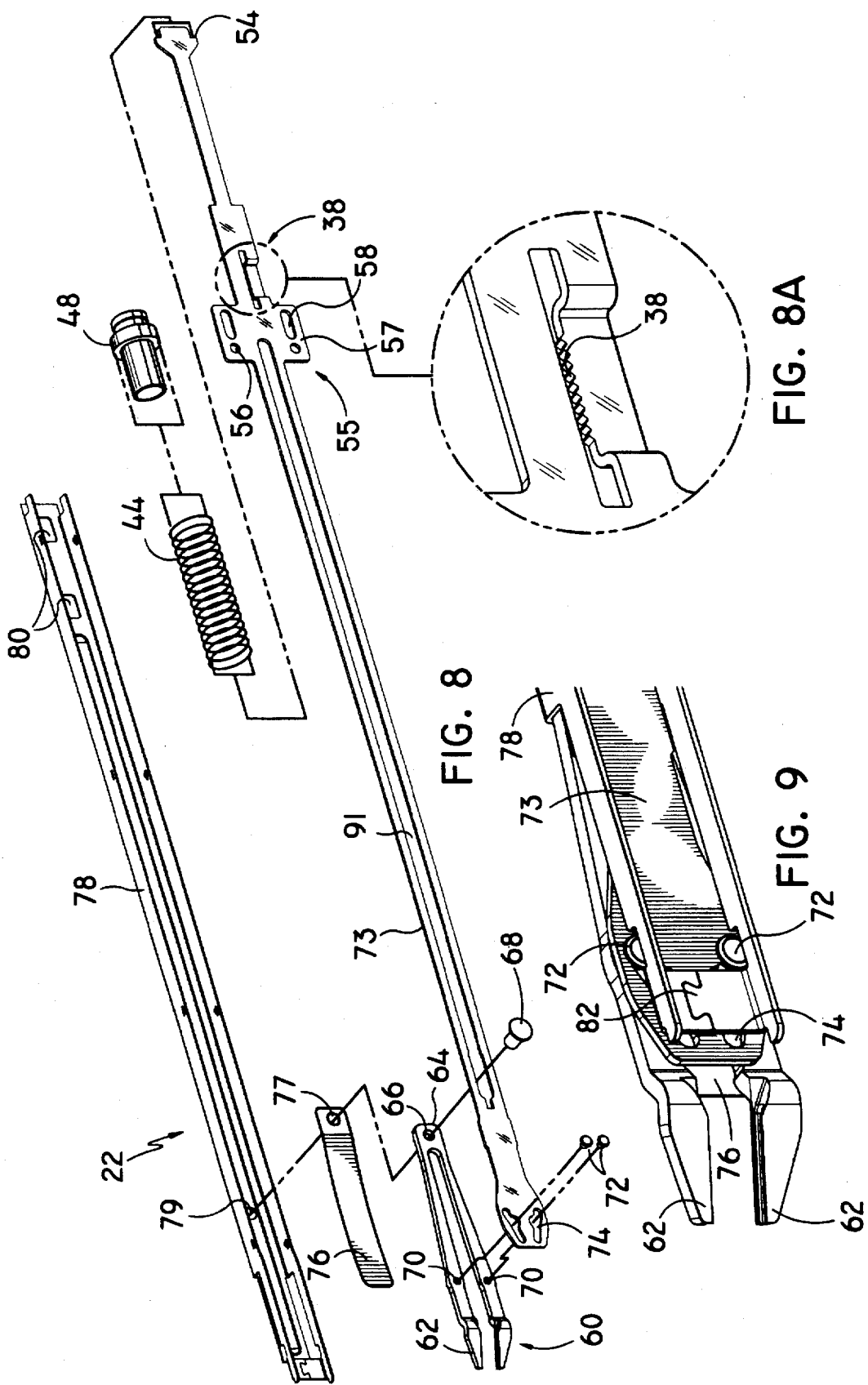

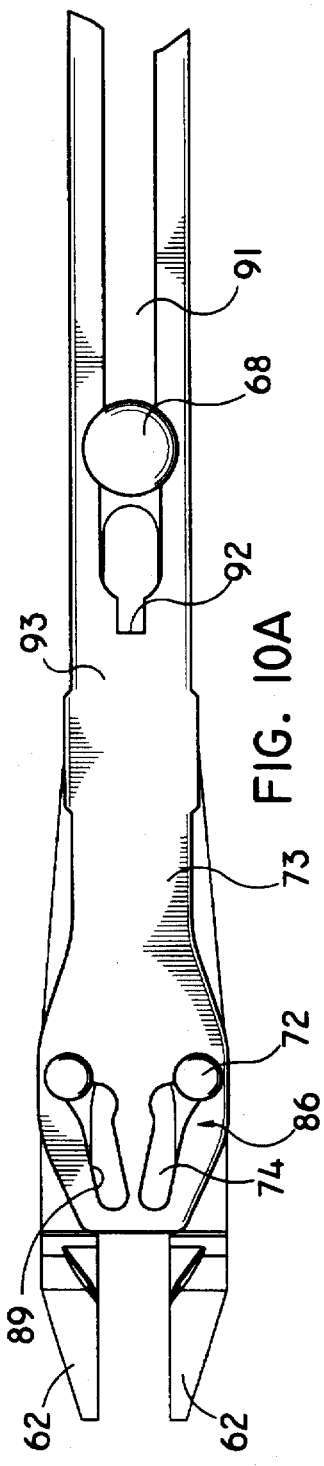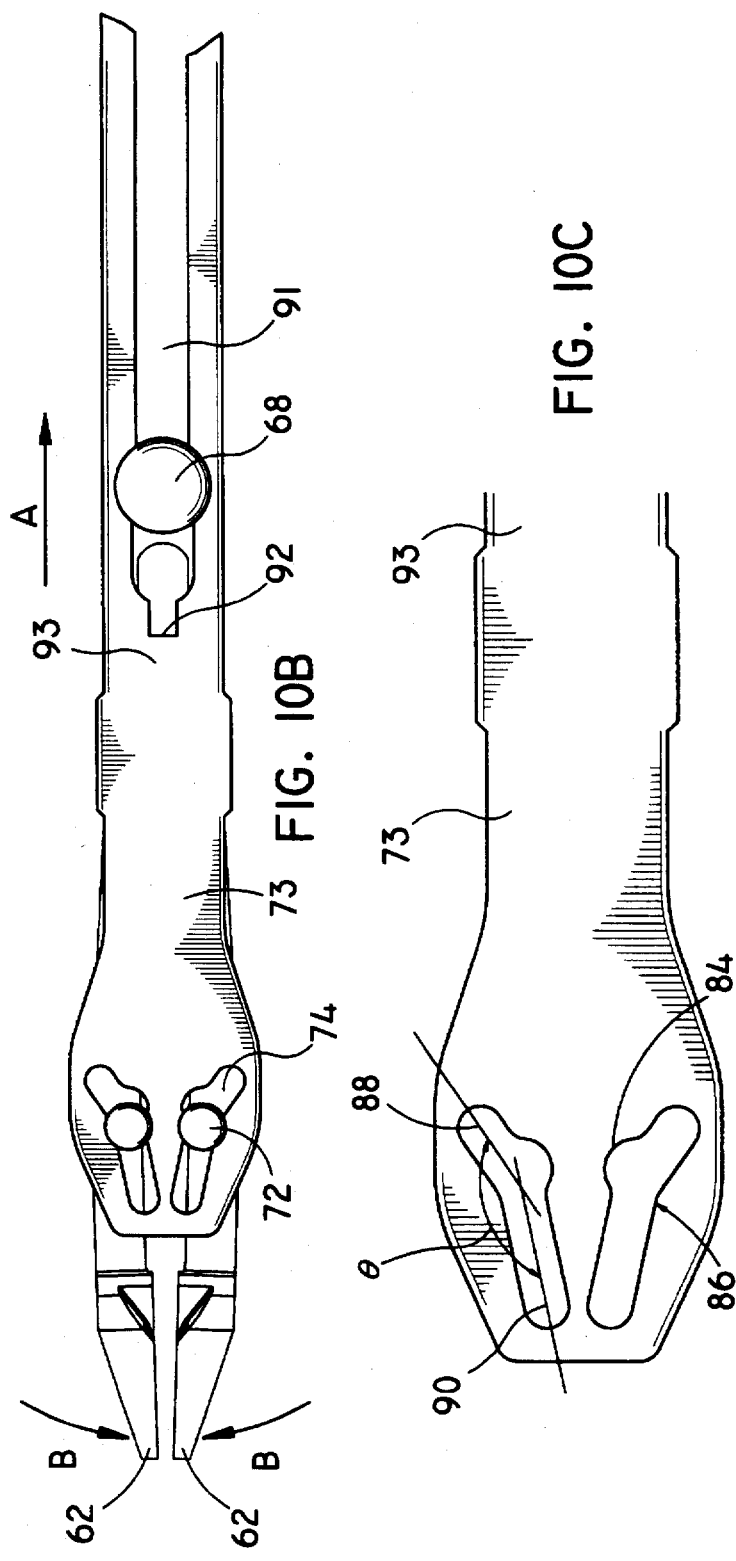

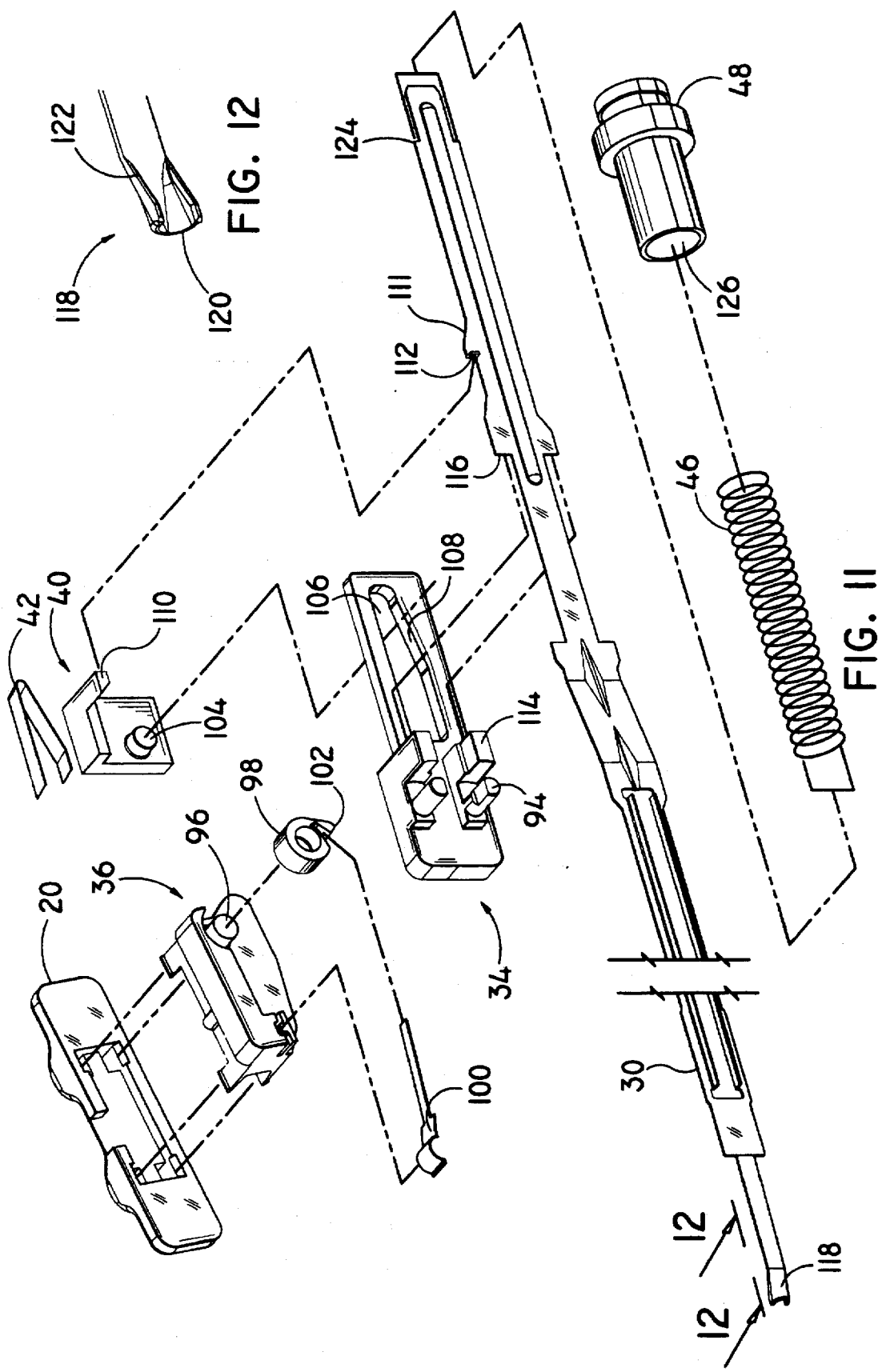

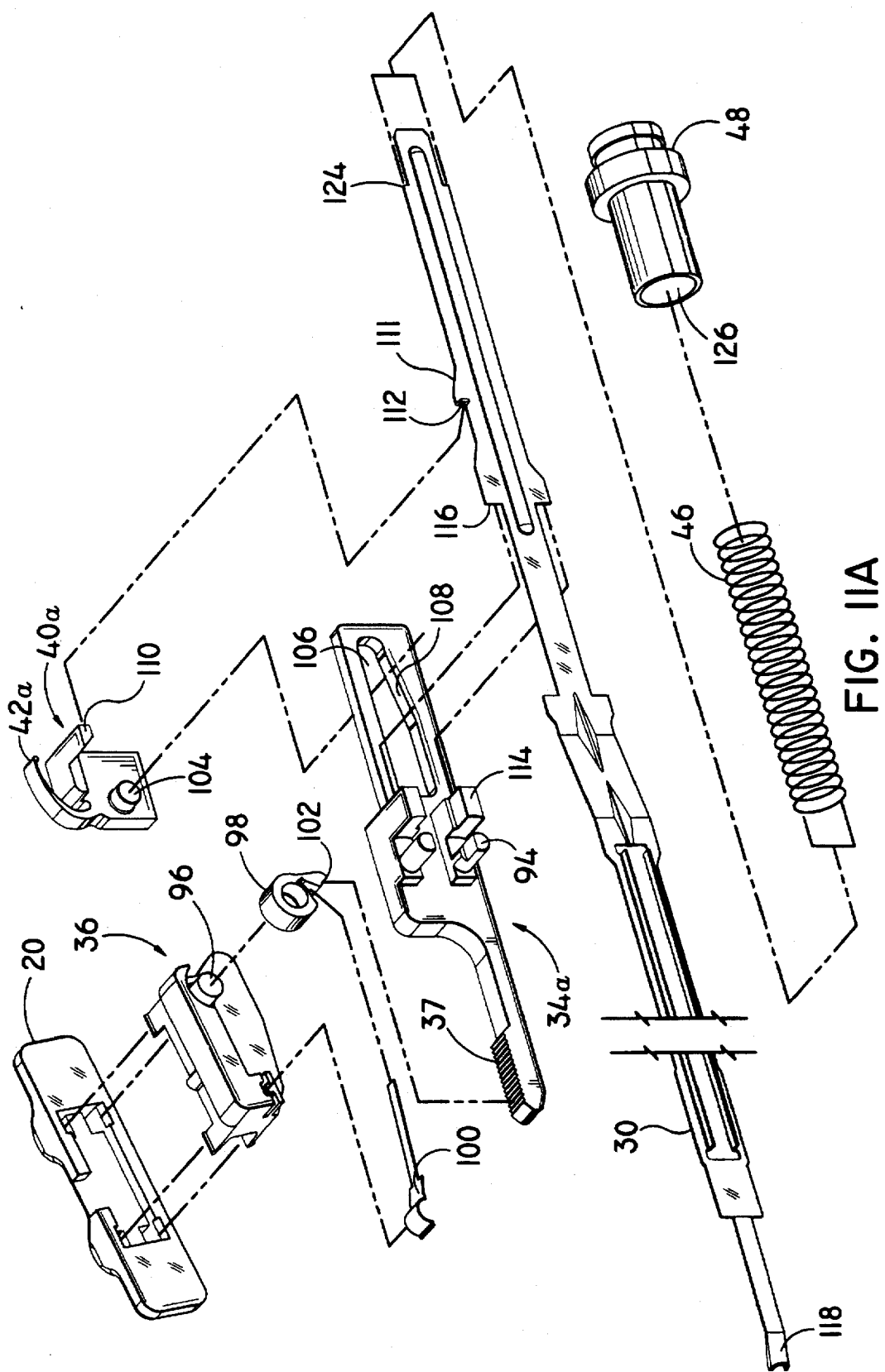

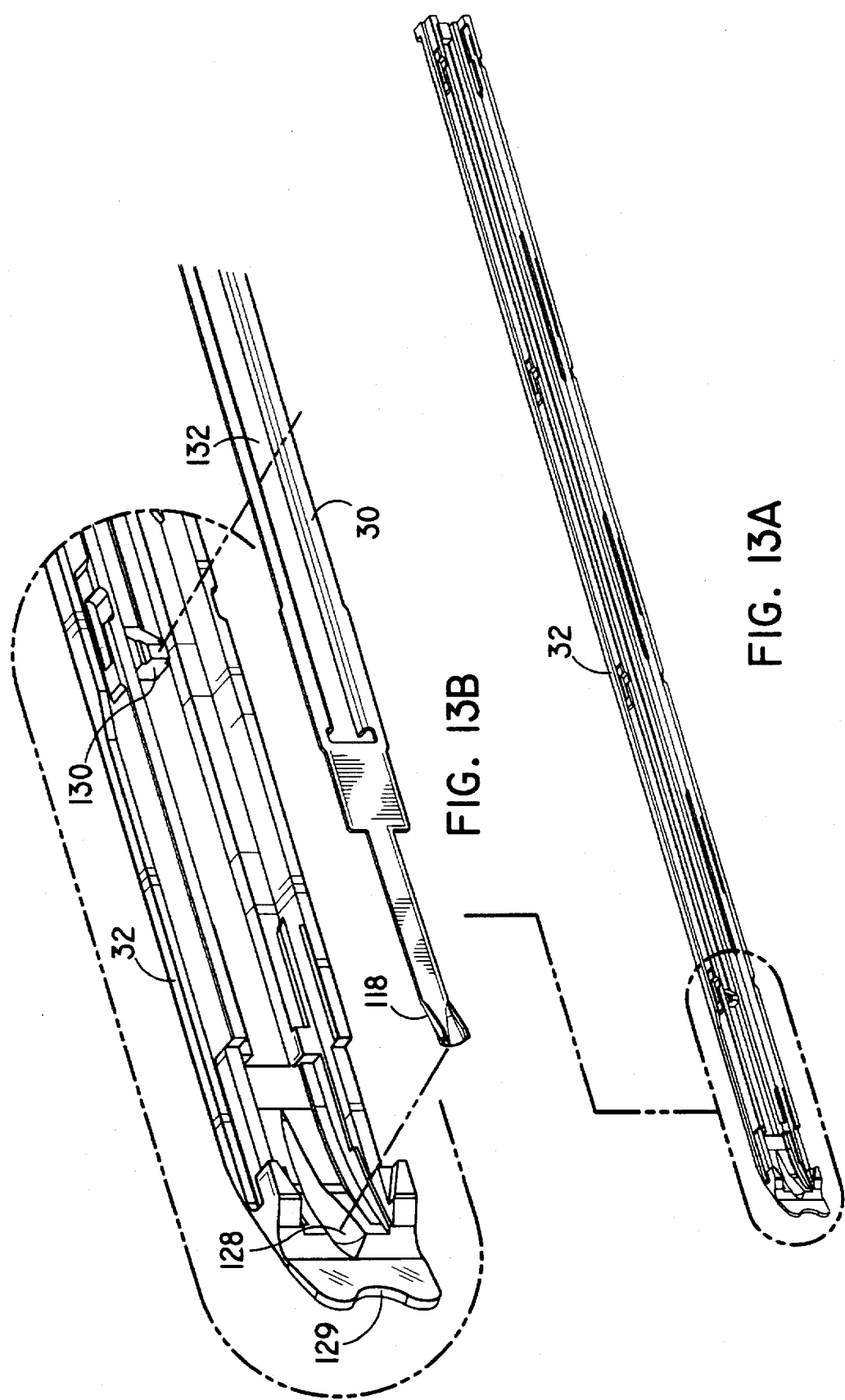

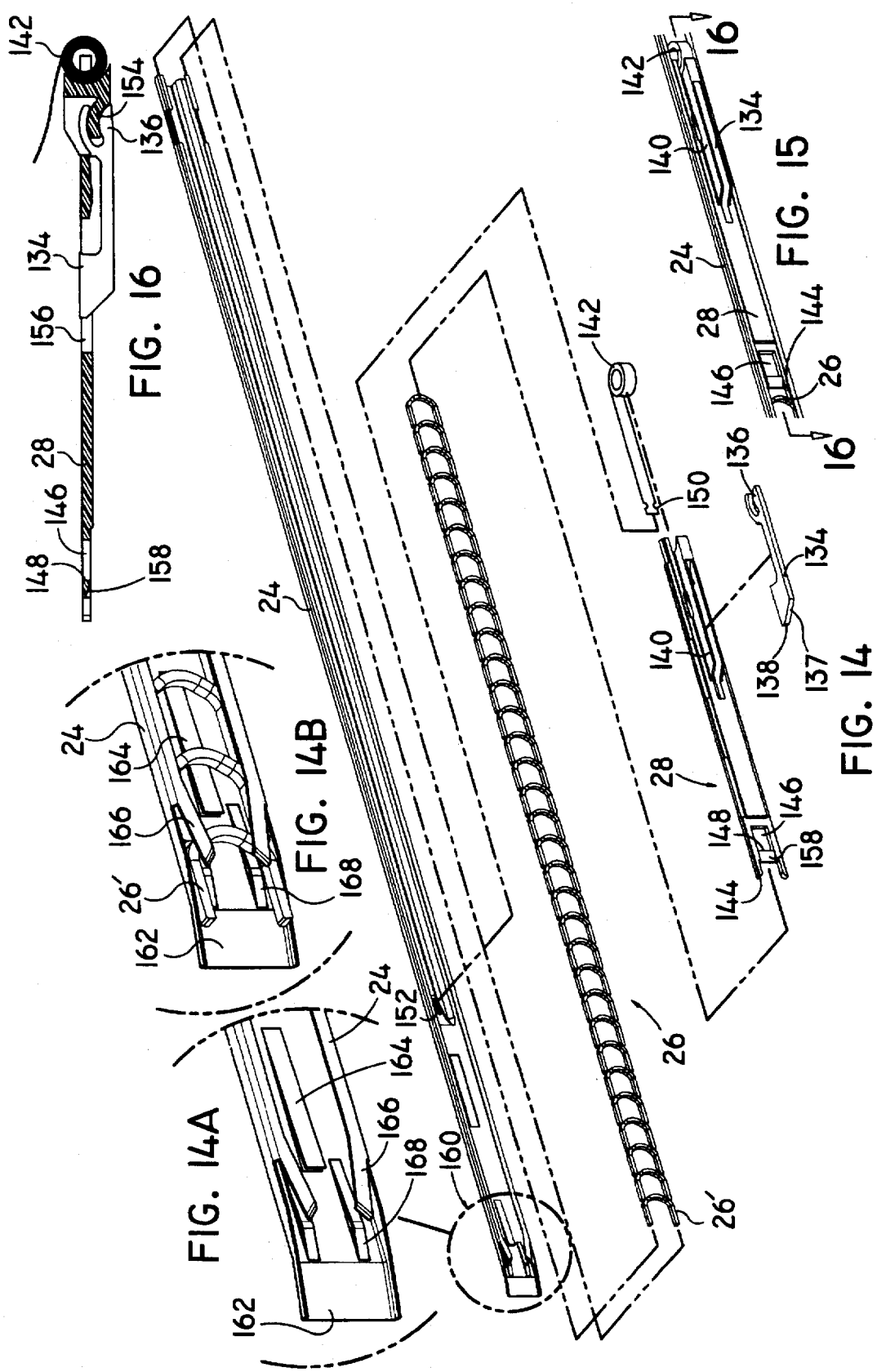

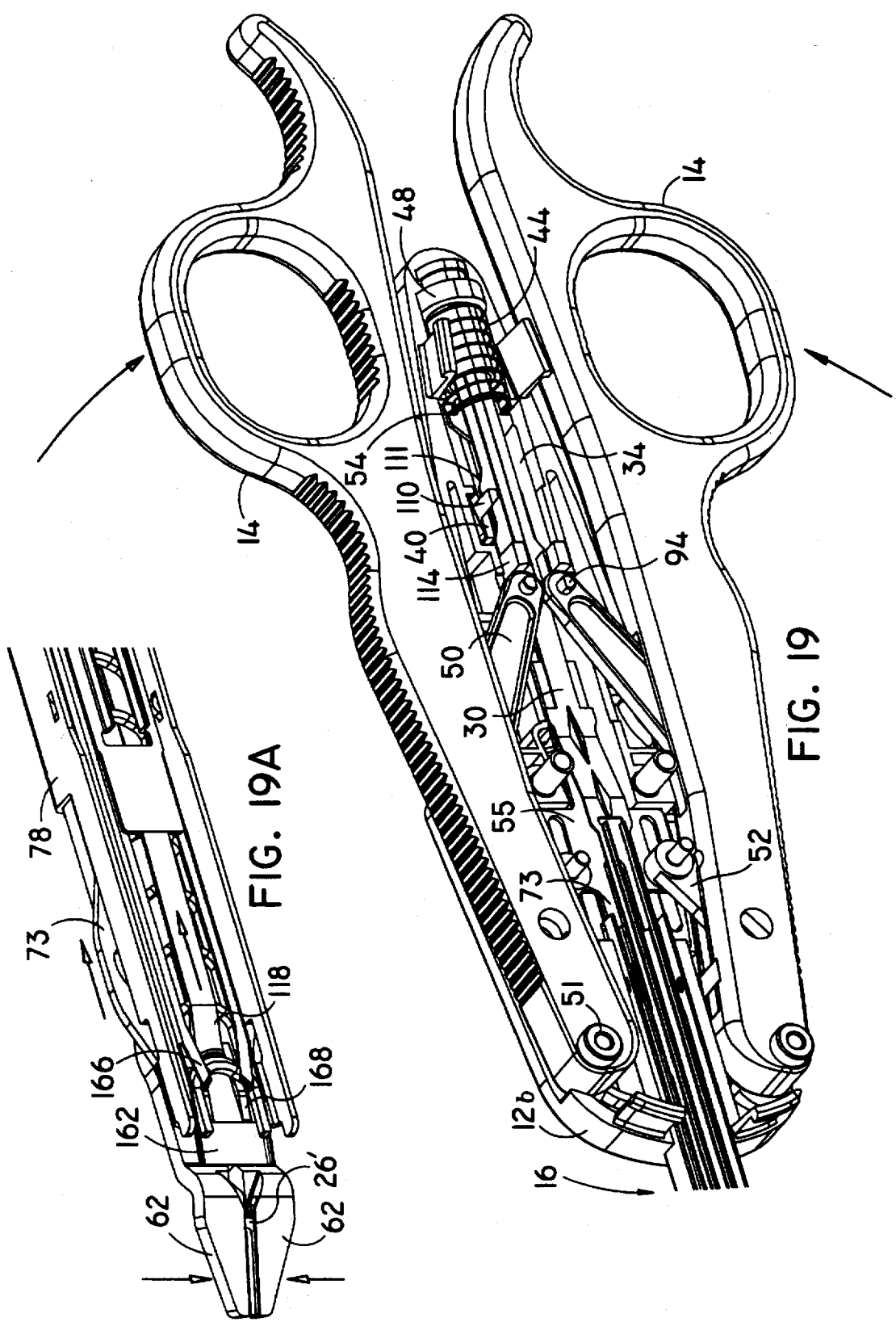

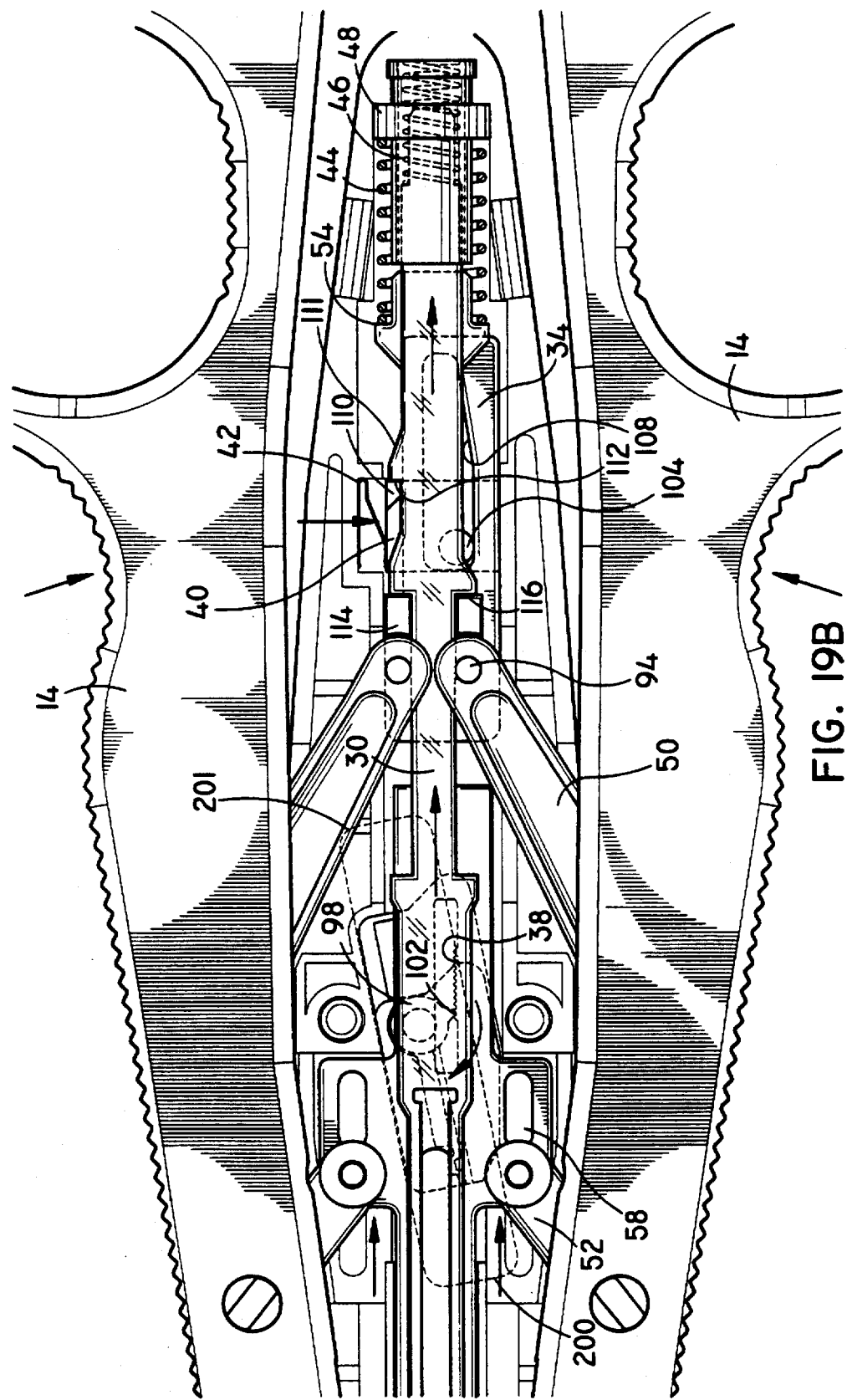

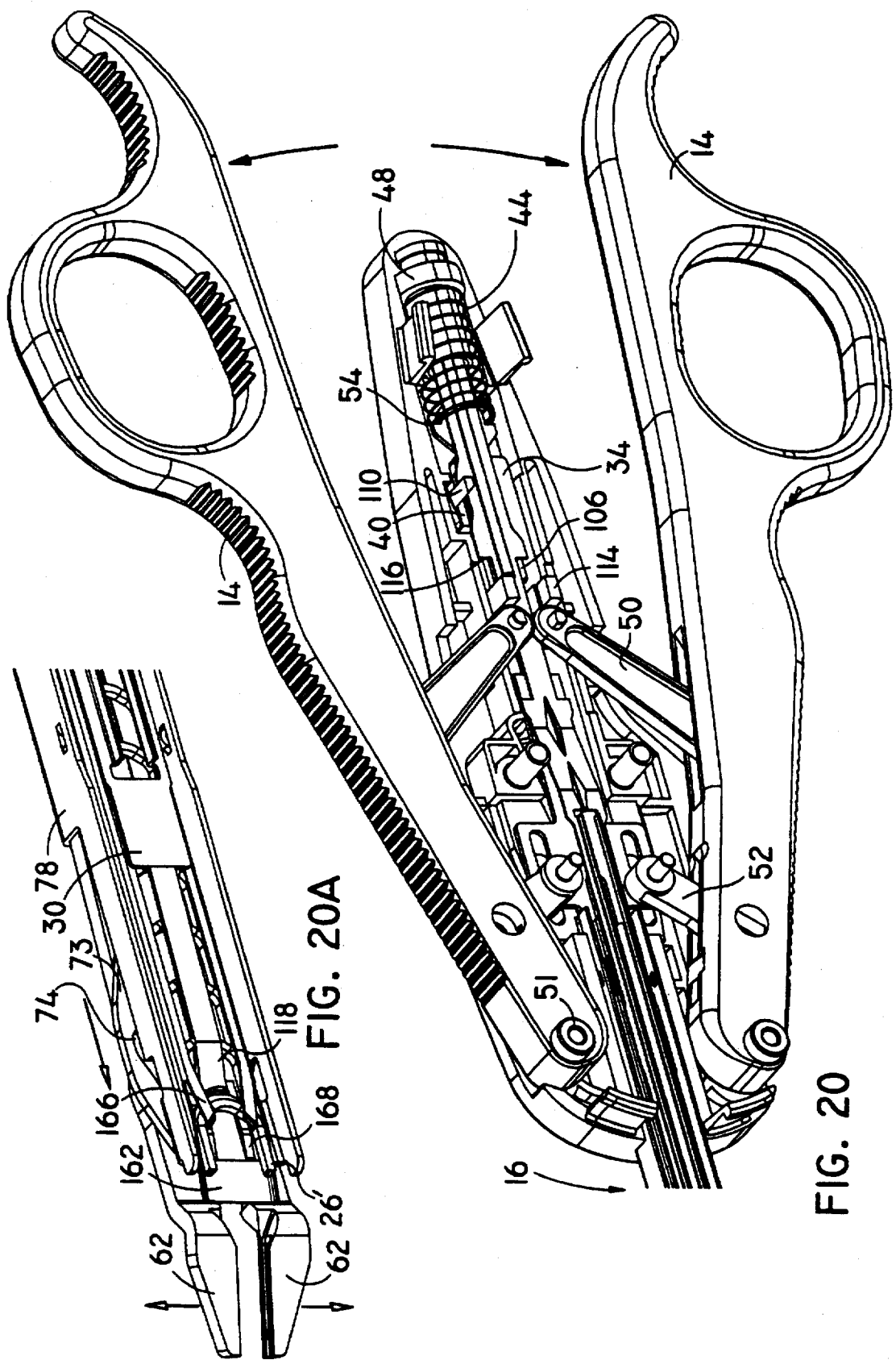

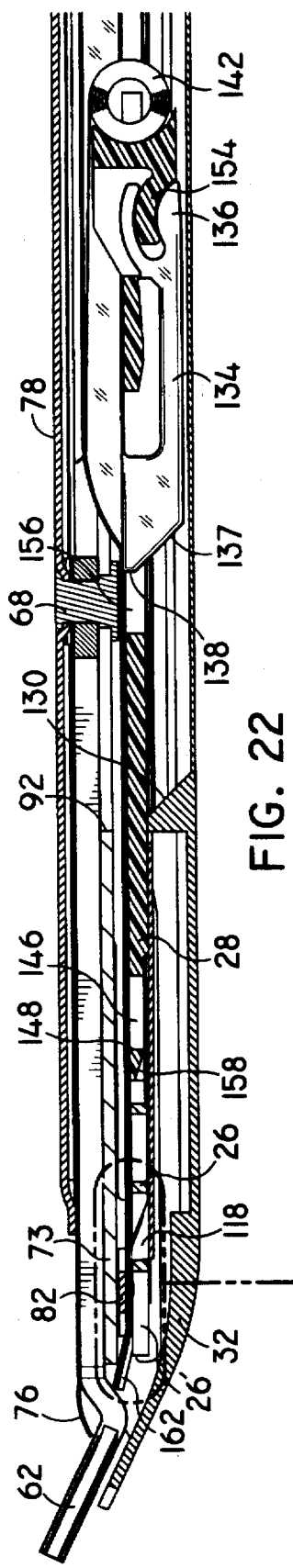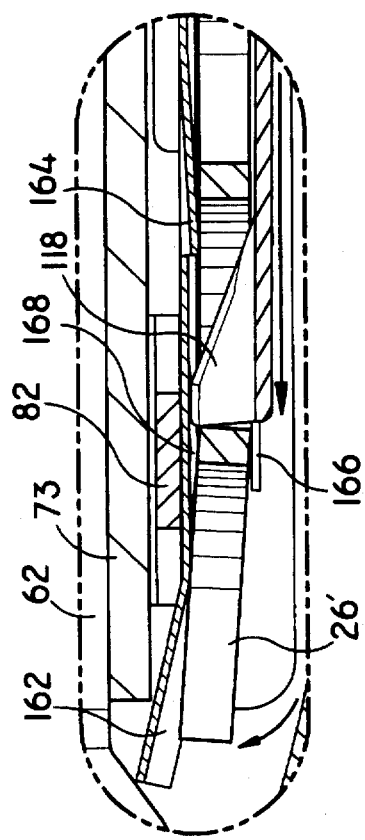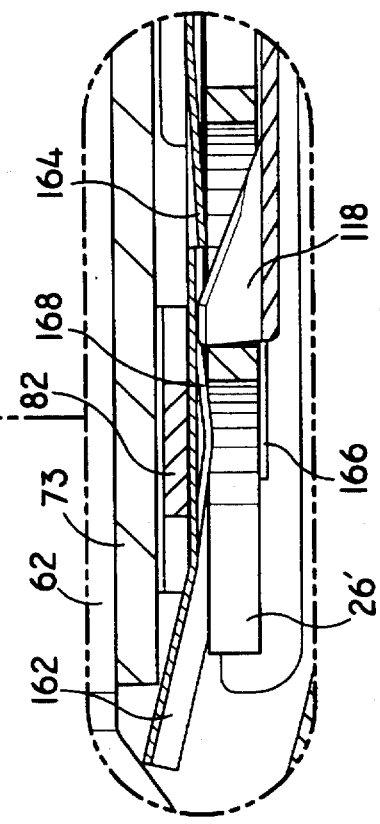
FIG. 22
FIG. 22A
FIG. 22B

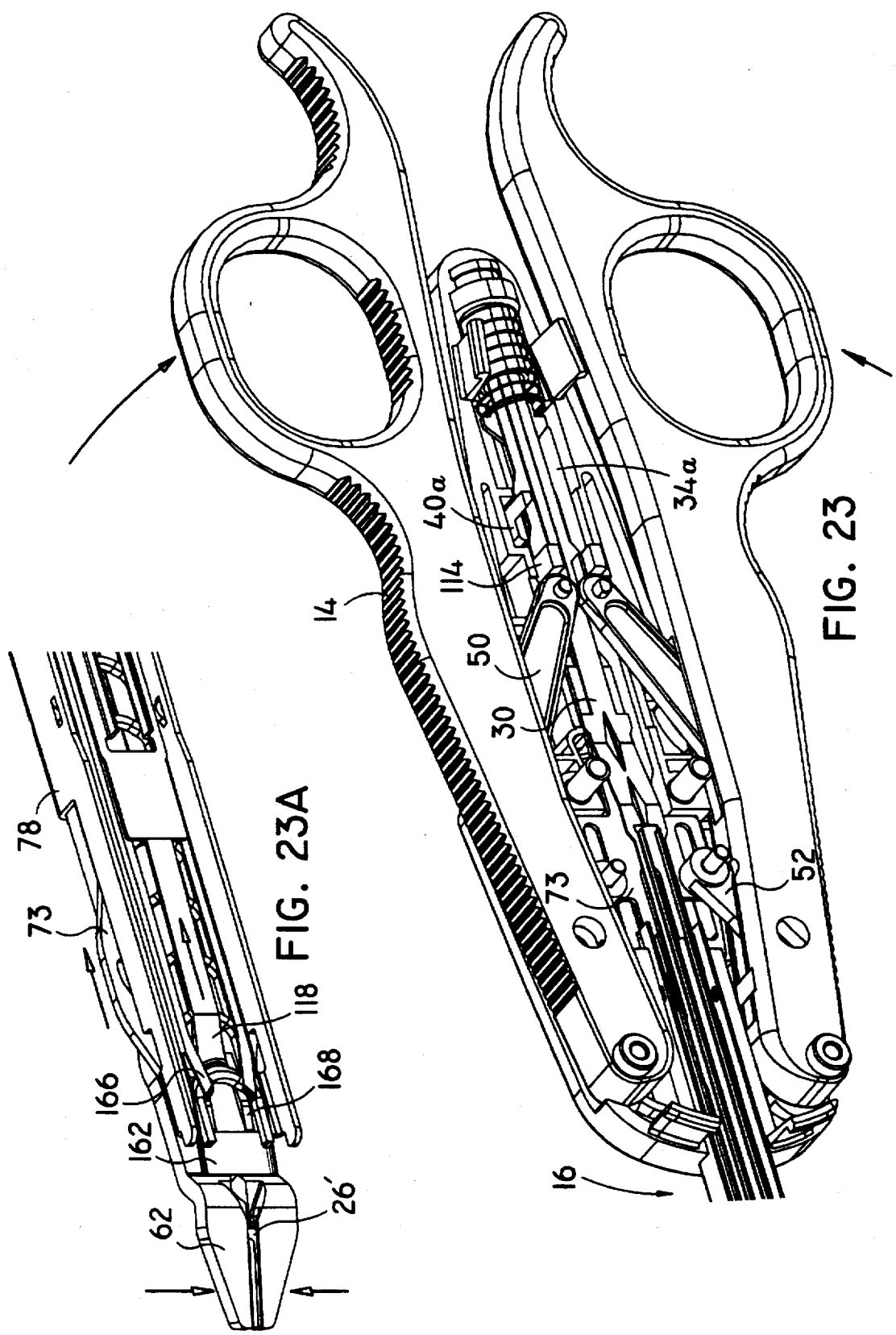

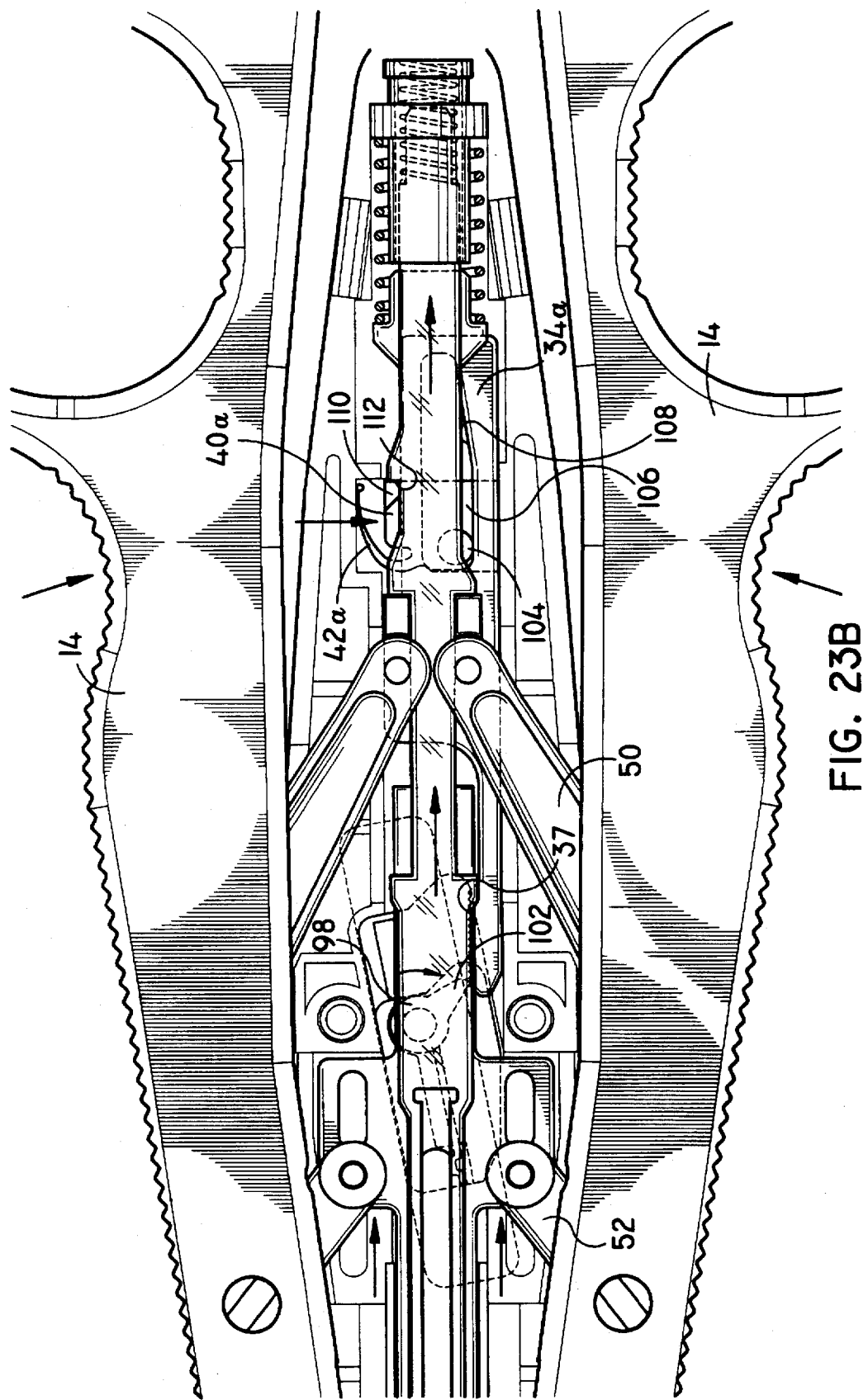

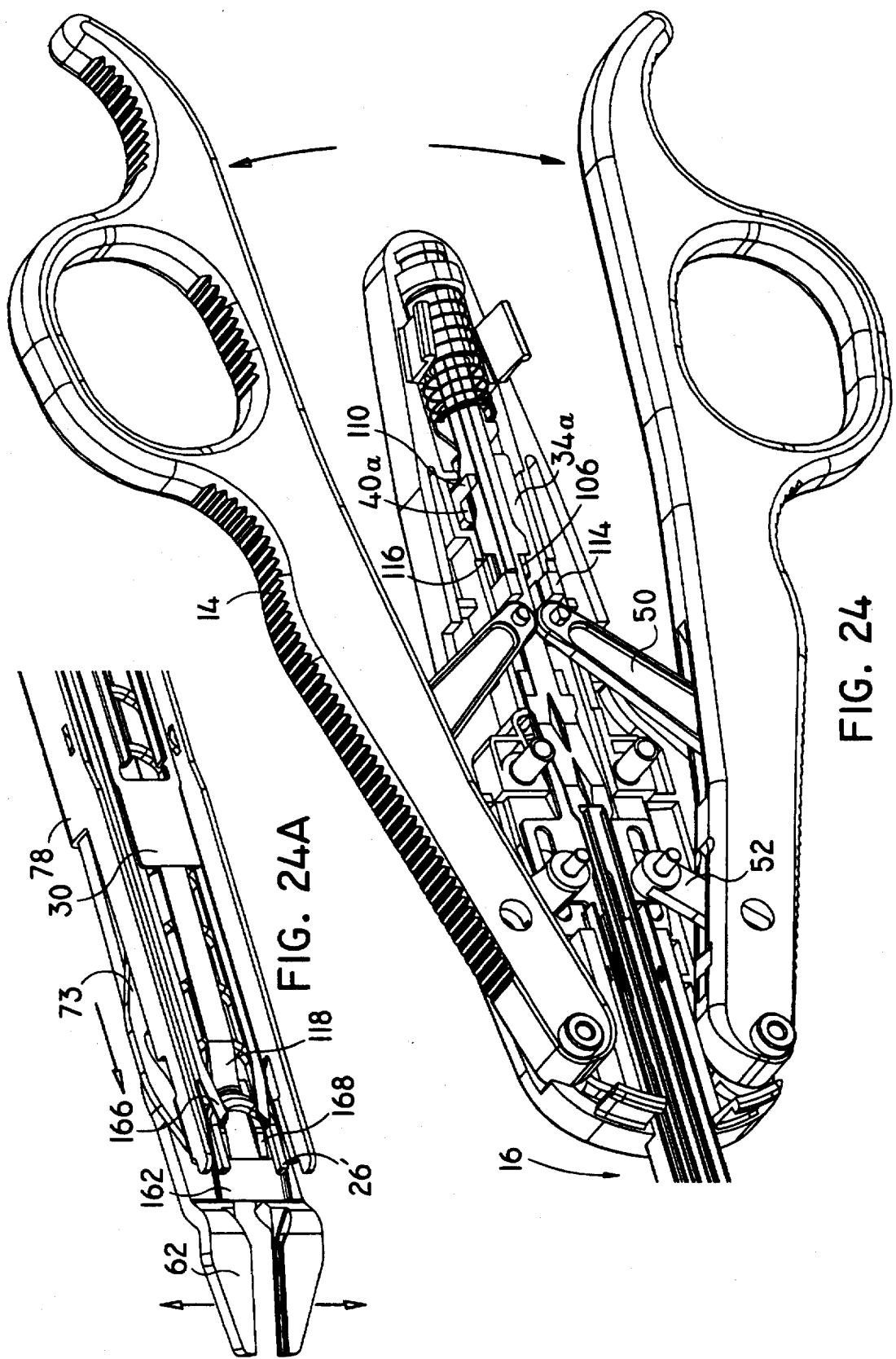

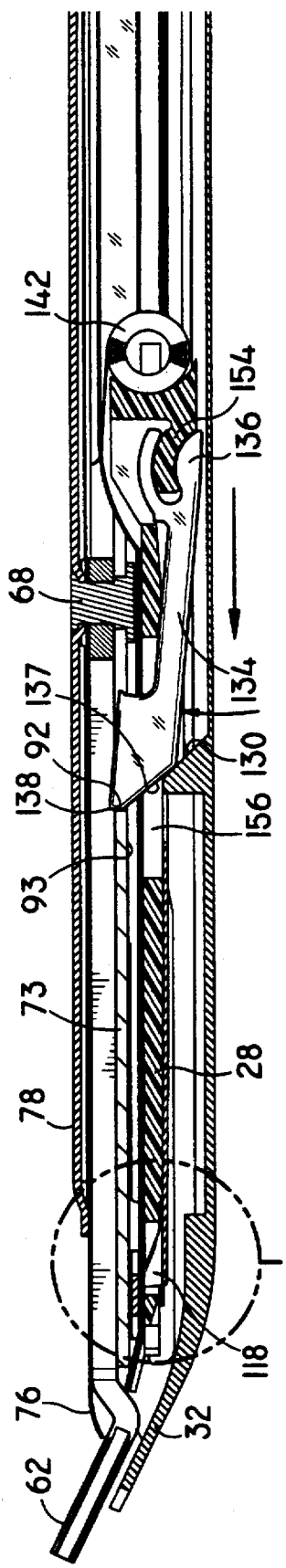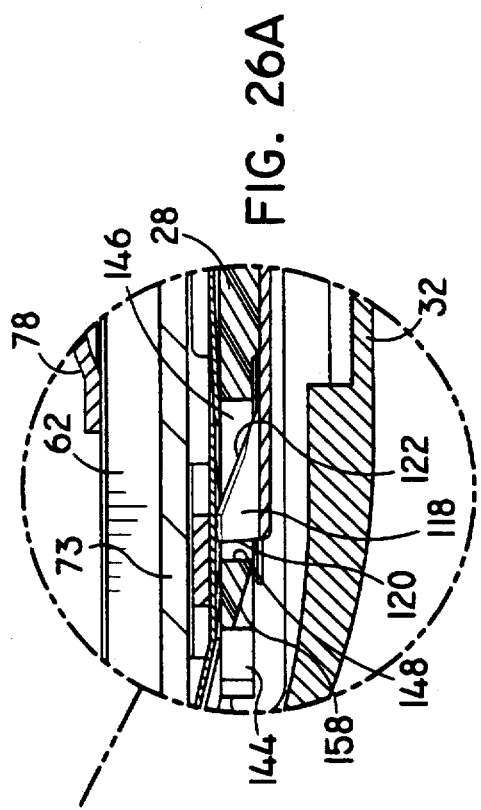
FIG. 26
FIG. 26A

SURGICAL CLIP APPLIER

BACKGROUND

1. Technical Field

The present application relates to surgical clip appliers, and in particular relates to instruments having a plurality of clips for applying the clips to body tissues and vessels during surgical procedures.

2. Discussion of the Prior Art

Surgical clip appliers are known in the art and have increased in popularity among surgeons by offering an alternative to conventional suturing of body tissues and vessels. Typical instruments are disclosed in U.S. Pat. No. 5,030,226 to Green et al. and U.S. Pat. No. 5,431,668 to Burbank, III et al. These instruments generally provide a plurality of clips which are stored in the instrument and which are fed sequentially to the jaw mechanism at the distal end of the instrument upon opening and closing of the handles at the proximal end of the instrument. As the handles are closed, the jaws close to deform a clip positioned between the jaw members, and as the jaws are opened to release the deformed clip, a new clip is fed from the series to a position between the jaws. This process is repeated until all the clips in the series of clips have been used.

Surgical clip appliers in the prior art are known to include some type of lockout mechanism which prevents closing of the handles, and consequentially closing of the jaws if there are no clips present in the instrument. These lockout mechanisms prevent closure of the jaws about tissue, which can traumatize the tissue and perhaps cause serious damage to the tissue or vessel when a clip is not present in the jaws. However, many of the prior art instruments provide a lockout mechanism which interferes with the closure of the jaws, and upon the application of enough force to the handles, the lockout mechanism many times may be defeated. In order to prevent this, complex mechanisms are often provided, resulting in increased cost of manufacture of the instrument.

In addition, many of the prior art instruments provide complex mechanical arrangements for closing the jaws while simultaneously preparing for feeding the next clip into the jaws after the clip positioned between the jaws is deformed and then released. These complex mechanisms, such as that shown in U.S. Pat. No. 5,431,668 to Burbank, III et al., require numerous parts which increases the cost of manufacture, as well as increasing the time it takes to assemble each instrument. In addition, these instruments generally drive a first component, such as the channel assembly, in one direction to close the jaws while simultaneously drawing the clip pusher bar in an opposite direction to prepare for feeding the next clip in the series of clips to the jaw mechanism. This arrangement typically requires additional moving parts, also tending to increase the cost of manufacture and increase the time of assembly.

The need therefore exists for an instrument for applying surgical clips which reduces the number of parts, and consequently reduces the cost of the instrument, while at the same time reducing the amount of time needed to assemble the instrument during manufacture. A specific need exists for an instrument which minimizes the number of moving parts and synchronizes the moving parts so that they move in the same direction upon closing and opening of the handles. By minimizing the number of moving pans, and synchronizing the direction of movement of the moving pans, the instrument becomes sturdier and easier to manipulate during the surgical procedure.

The need also exists for an instrument having a lockout mechanism which both prevents closing of the jaws by providing a reliable blocking mechanism, while at the same time providing a mechanism for rendering the instrument inoperable upon the application of a predetermined force to the handles after all the clips in the instrument have been utilized during the surgical procedure.

SUMMARY

A surgical clip applier is disclosed which is both highly efficient and reliable, and which reduces the number of parts which make up the instrument to provide a low cost, easy to assemble instrument. The instrument synchronizes the direction of movement of the moving parts of the instrument upon opening and closing of the handles, resulting in a sturdier and more reliable clip applier.

The surgical clip applier includes a housing at a proximal end of the instrument, with a pair of handles pivotably attached to the housing on opposite sides of the instrument. A channel assembly or body portion extends from the housing and is fixedly secured thereto. The channel assembly terminates in a jaw assembly which includes a pair of jaw members which are fixedly secured to the distal end of the channel assembly. Neither the channel nor the jaws move during opening and closing of the handles with respect to a longitudinal axis of the instrument, as defined by the channel assembly.

The handles are secured to the housing at a pivot point, and further include a pair of links connecting each handle to the movable components positioned within the housing. A first link connects each handle to a cam plate which is slidably positioned in the channel assembly and which is operably connected to the jaw members for opening and closing the jaw members as the handles open and close. A second link is provided on each handle and is connected to a drive plate which controls the movement of a clip pusher bar, which itself is slidably positioned within the channel assembly and terminates adjacent the jaw members. Also positioned within the channel assembly is a plurality of clips arranged in series relation on a clip carrier. The series of clips is urged distally towards the jaw members by a clip follower which is biased in the distal direction by a constant force spring.

It is desirable for the clip applier to have a clip initially stored between the jaw members so that the clip applier is ready to use after it is removed from its package. Alternately, the instrument may be packaged with the handles already in the closed position, so that as the instrument is removed from the package, the handles open to advance a clip to the jaws, as described below, and the instrument is ready to use. As the jaws are positioned about tissue, or about a hollow vessel such as a body duct or blood vessel, the surgeon squeezes the handles to move the handles from the open position to the closed position. As this occurs, the first link on the handles causes the cam plate to move in a proximal direction against the biasing of a cam plate spring positioned in the housing. The distal end of the cam plate preferably includes a pair of slots each of which are angled in a direction towards the longitudinal axis of the instrument. The jaw members preferably include a pair of upstanding rivets which are positioned in the slots on the cam plate, such that when the cam plate is drawn in a proximal direction upon closing of the handles, the rivets ride in the slots and function to close the jaws to deform the clip positioned between the jaws.

As the handles are closed, the second link on the handles serves to move the clip pusher bar in a proximal direction against the biasing of a pusher bar spring. At the distal end of the instrument, the nose portion of the pusher bar is moved into position behind the distalmost clip in the series of clips and is ready to feed the next clip to the jaws. As the pusher bar is moved in the proximal direction, upon completion of the closing stroke of the handles, the pusher bar is latched by a spring biased latch member in the housing so that the nose portion is held in position behind the distalmost clip.

As the handles are released, the cam plate moves distally under the biasing of the cam plate spring in the housing, and the distal movement of the cam plate permits the jaw rivets to ride in the cam plate slots to force the jaws open, thus releasing the deformed clip from between the jaws. The pusher bar is latched and is held against forward movement for a delay period until the handles and jaws are completely opened, at which time the latch is released and the pusher bar is moved in a distal direction under the influence of the biasing spring. As the pusher bar moves in the distal direction, the nose portion of the pusher bar feeds the distalmost clip from the series of clips into the jaw members.

The clip applier thus accomplishes the crimping and feeding process by maintaining the channel assembly and the jaw members in a stationary position with respect to the longitudinal axis, thereby adding stability and strength to the instrument. The clip applier also provides for synchronized movement of all components in a first direction, i.e. moving the cam plate and clip pusher bar in a proximal direction during deformation of a clip that is positioned between the jaw members, and then moving all movable components in a distal direction to open the jaws and feed the distalmost clip from the series of clips to the jaws for the next clip applying procedure.

A novel lockout mechanism is also provided which ensures that the instrument will not operate after the last clip in the series of clips has been deformed and released from the instrument, and ensures that the instrument is rendered inoperable through the provision of a novel destructive lockout mechanism. The clip applier thus provides a lockout mechanism which is in effect a three-way lockout when the series of clips has been spent.

The lockout mechanism utilizes the clip follower, which urges the series of clips in a distal direction through the clip carrier under the influence of a constant force spring, to prevent movement of both the cam plate and the pusher bar member after all the clips are spent. The cam plate itself also includes a novel mechanism for rendering the instrument inoperable through the provision of a frangible portion on a part of the cam plate which is located in the housing.

Once all the clips have been spent from the series of clips, the lockout mechanism blocks movement of the pusher bar member and the cam plate at the distal end of the instrument. If the user tries to close the handles at this point, in an attempt to defeat the lockout mechanism at the distal end of the instrument, the frangible portion of the cam plate located within the housing will rupture, thus disengaging the handle from the cam plate, and rendering the instrument useless. This ensures that no damage can be done to tissues or vessels if the surgeon inadvertently tries to close the handles after the clips have all been utilized.

The surgical clip applier may also be provided with a selectable ratchet mechanism located on the housing which permits the surgeon to incrementally close the jaws about a vessel or a shunt positioned in a tubular vessel, thus permitting the application of partially closed clips. The instrument may also be operated without the ratchet, simply by disengaging the ratchet mechanism prior to operation.

BRIEF DESCRIPTION OF THE DRAWINGS

The present clip applier will be more fully appreciated as the same becomes better understood from the following detailed description when considered in connection with the following drawings, in which:

FIG. 3 illustrates a bottom plan view of the clip applier;

FIG. 4 illustrates a side plan view of the clip applier;

FIG. 8 illustrates an exploded perspective view of the channel subassembly of the clip applier of FIG. 7;

FIG. 8A illustrates an enlarged perspective view showing in detail the rack portion of the ratchet mechanism of the clip applier of FIG. 8;

FIG. 9 illustrates an enlarged perspective view of the distal end of the assembled channel subassembly of FIG. 8;

FIGS. 10A and 10B illustrate an enlarged plan view of the cam plate and jaw assembly showing the closing operation of the jaw assembly;

FIG. 10C illustrates an enlarged plan view of the distal end of the cam plate;

FIG. 11 illustrates an exploded perspective of the clip pusher bar subassembly as well as the selectable ratchet mechanism;

FIG. 11A illustrates an exploded perspective view of the pusher bar subassembly and an alternate embodiment of the ratchet mechanism;

FIG. 12 illustrates an enlarged perspective view of the nose portion of the pusher bar taken along lines 12—12 of FIG. 11;

FIGS. 13A and 13B illustrate a perspective view of the channel cover with respect to the pusher bar member;

FIG. 14 illustrates an exploded perspective view of the clip carrier subassembly which includes the series of clips and the clip follower;

FIGS. 14A and 14B illustrate an enlarged perspective view of the distal end of the clip carrier showing the clip carrier with and without clips loaded thereon, respectively;

FIG. 15 illustrates a partial perspective view of the clip carrier subassembly showing the clip follower in position behind the series of clips;

FIG. 16 illustrates a side cross-sectional view of the clip follower taken along lines 16—16 of FIG. 15;

FIG. 19 illustrates a perspective view of the handle of the clip applier, with the top cover removed, showing the components in the housing as the handles are closed;

FIG. 19A illustrates a perspective view of the distal end of the instrument with the channel cover removed, showing the position of the jaws corresponding to the position of the handles as shown in FIG. 19;

FIG. 19B illustrates a top plan view of the housing with the top housing removed showing the position of the components with the handles in the closed position corresponding to FIG. 19;

FIG. 20 is a perspective view of the housing with the top housing removed showing the position of the components when the handles are in the opening stroke;

FIG. 20A illustrates a perspective view of the distal end of the instrument with the channel cover removed showing the position of the components when the handles are in the position shown in FIG. 20;

FIG. 22 illustrates the distal end of the channel assembly in cross-section;

FIGS. 22A and 22B illustrate an enlarged cross-sectional view of the detail of FIG. 22 showing the distalmost clip in the series of clips prior to feeding to the jaw members and during the feeding process, respectively;

FIGS. 23–25 illustrate the operation of the instrument as described with respect to FIGS. 19–21 with an alternate embodiment of the ratchet mechanism;

FIG. 26 illustrates a cross-sectional view of the distal end of the channel assembly showing the dual lockout mechanism of the clip applier; and FIG. 26A illustrates an enlarged cross-sectional view of the detail of FIG. 26.

DETAILED DESCRIPTION OF THE PREFERRED EMBODIMENT

Figure 1:
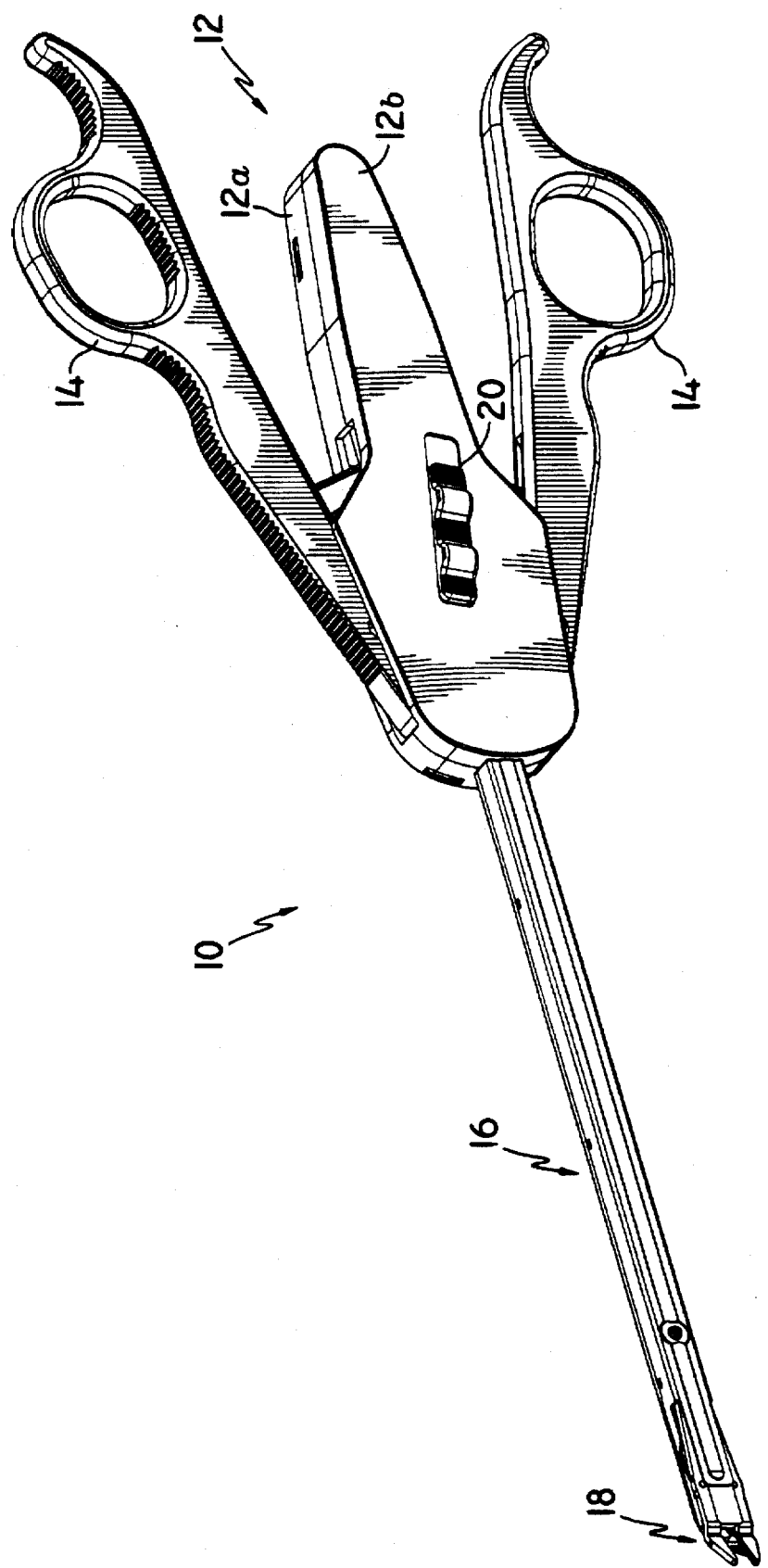
FIG. 1 illustrates a perspective view of the clip applier showing what is considered the bottom of the instrument.
Figure 2:
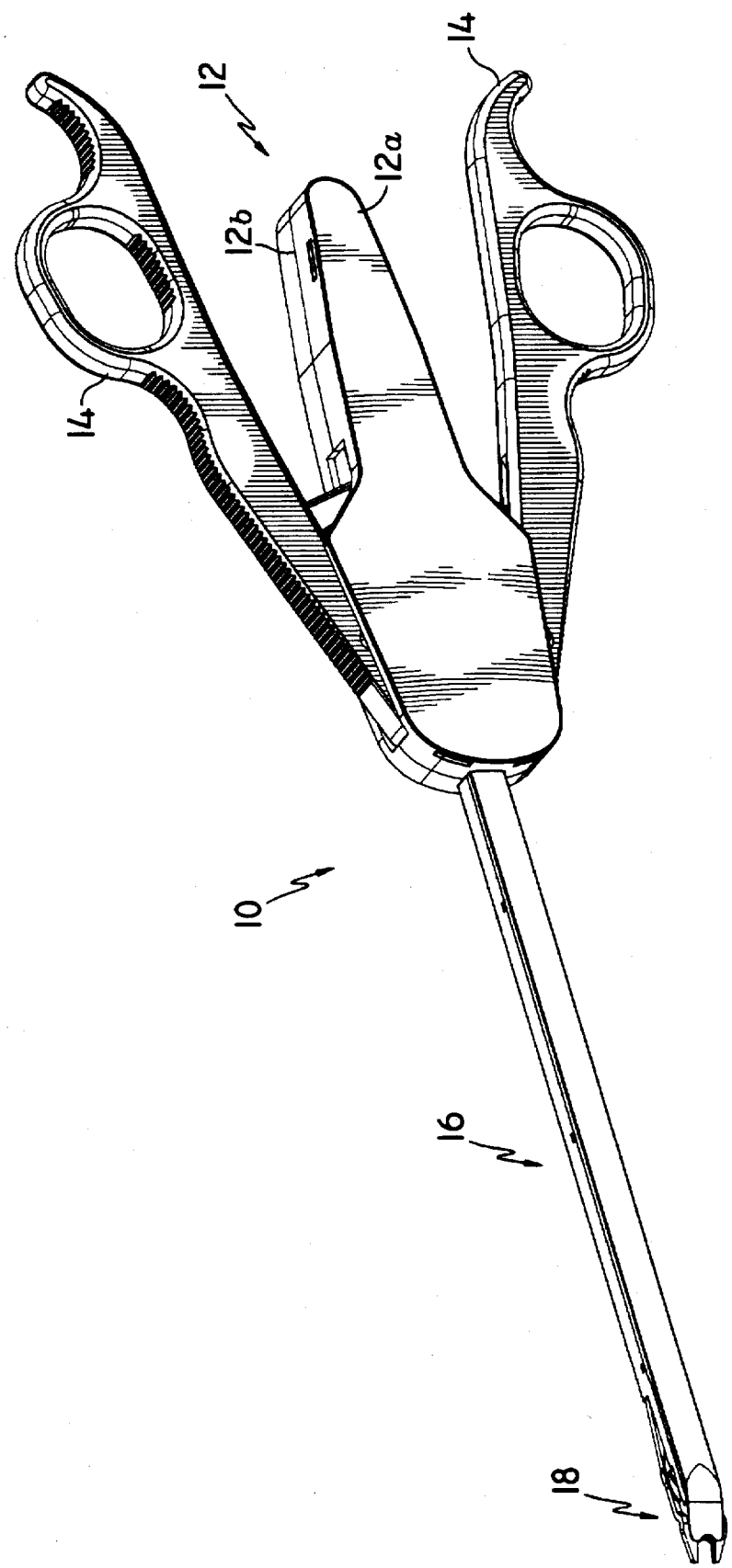
FIG. 2 illustrates a perspective view of the clip applier showing what is considered to be the top of the instrument.
Figure 5:
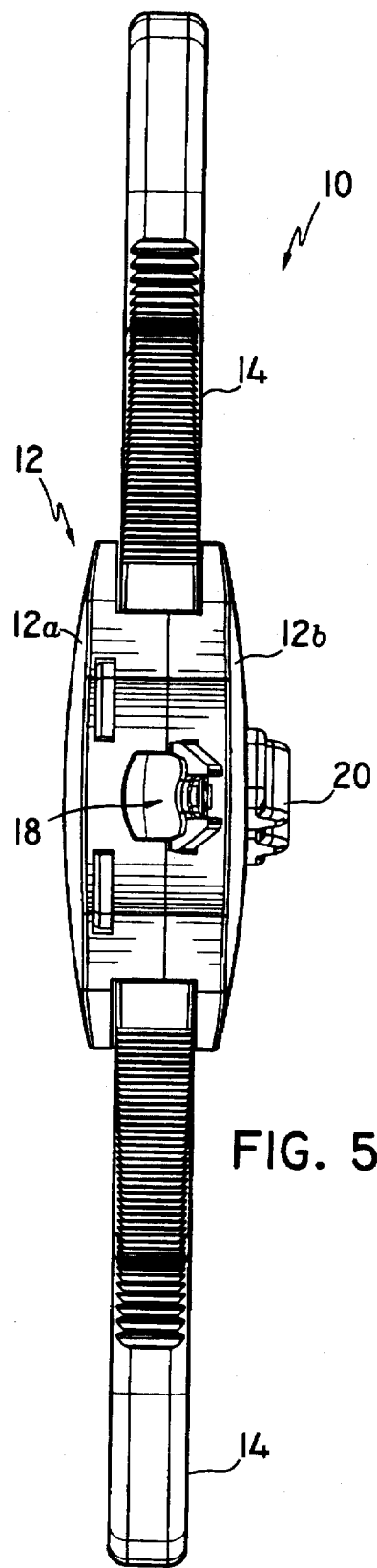
FIG. 5 illustrates a front plan view of the clip applier.
Figure 6:
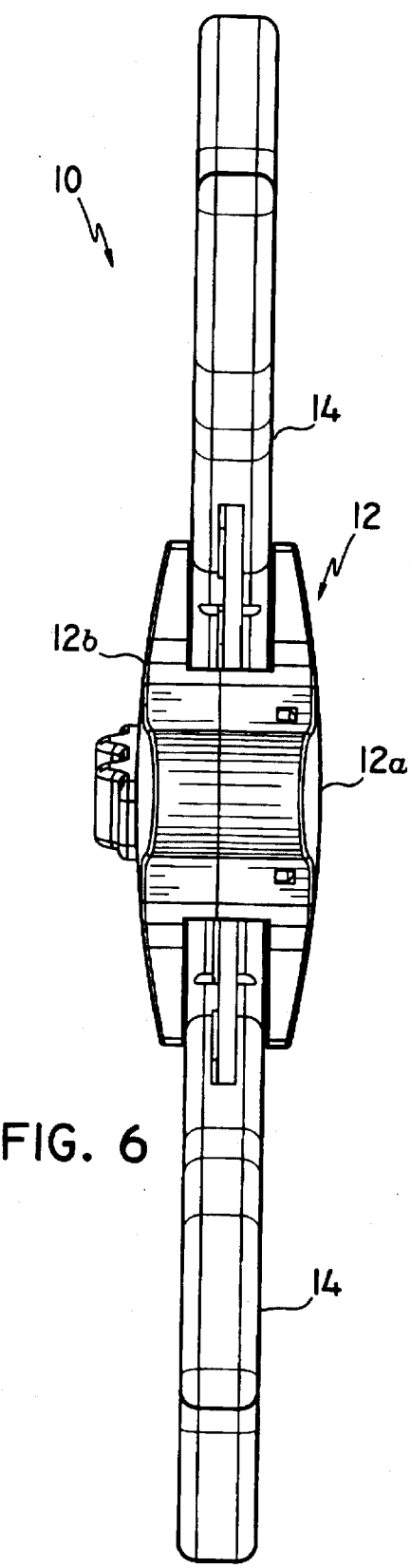
FIG. 6 illustrates a rear plan view of the clip applier.

Referring now to the drawings, in which like reference numerals identify similar or identical elements throughout the several views, and referring in particular to FIGS. 1–6, the surgical clip applier 10 includes a housing 12 having an upper housing half 12a and lower housing half 12b. A pair of handles 14 are pivotably secured to the housing 12 and extend outwardly therefrom. A channel assembly 16 is fixedly secured to the housing 12 and extends outwardly therefrom, terminating in a jaw assembly 18. A ratchet button 20, whose function will be described below, is provided on housing 12 for selectively engaging and disengaging the ratchet mechanism positioned within the housing.

Figure 7:
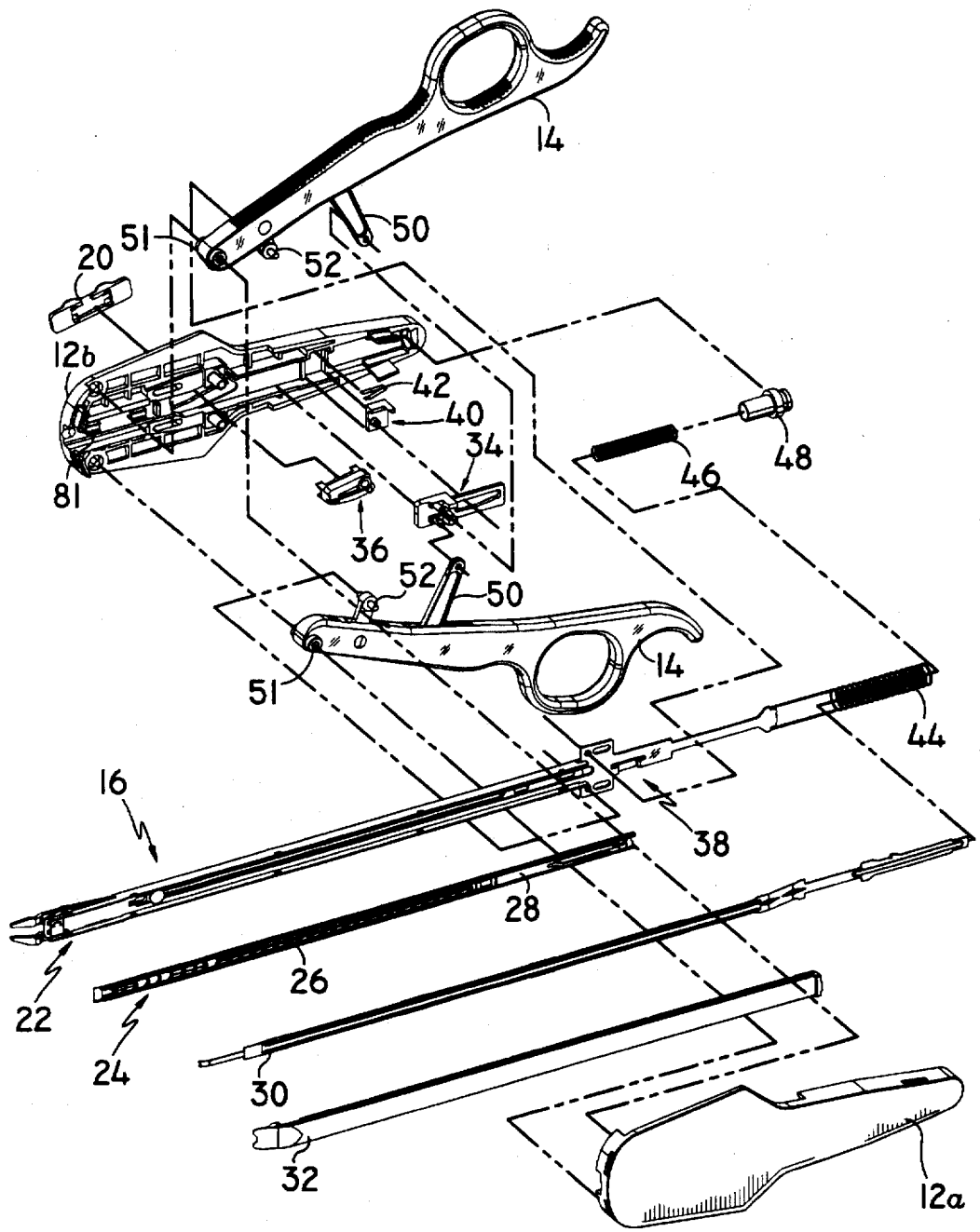
FIG. 7 illustrates an exploded perspective view of the clip applier.

Referring now to FIG. 7, there is illustrated an exploded perspective view of clip applier 10 which shows the components of the instrument. Housing halves 12a and 12b preferably fit together by snap fit although any suitable method for securing the handle halves together in a conventional manner is acceptable. Channel assembly 16 includes channel subassembly 22, and clip carrier 24 which includes a plurality of clips 26 which are urged towards the jaw assembly 18 by clip follower 28. Clip pusher bar 30 is also positioned in channel assembly 16 and is enclosed within the channel assembly 16 by channel cover 32. The channel assembly 16 is secured to housing 12 through the provision of channel mounting slots 80, as best seen in FIG. 8, which fit onto channel mounting posts 81 which are positioned within the housing. This post and slot arrangement fixedly secures the channel 78 of channel assembly 16 to the housing.

Also positioned within housing 12, is drive plate 34 which controls movement of the clip pusher bar 30. Drive plate 34 cooperates with latch plate 40 and latch spring 42 to control the movement of pusher bar 30 in a distal direction for feeding clips to the jaw assembly. Cam plate spring 44 and pusher bar spring 46 are assembled with spring sleeve 48 to bias the cam plate and pusher bar, respectively in a distal direction. Also included within housing 12 is a ratchet mechanism, having rack 38, as best seen in FIG. 8A, preferably positioned on cam plate 73, which is engaged by pawl 98 (as seen in FIG. 11) which is mounted on ratchet slide 36. Ratchet slide 36 is controlled by ratchet button 20 which serves to move pawl 98 into or out of engagement with rack 38.

Handles 14 are secured to housing 12 by handle pivot posts 51. A pair of link members 50 and 52 are provided, where pusher bar link 50 is connected to drive plate 34 to control the movement of pusher bar 30, while cam plate link 52 is secured to cam plate 73 to control the movement of the cam plate 73.

Figure 7A:
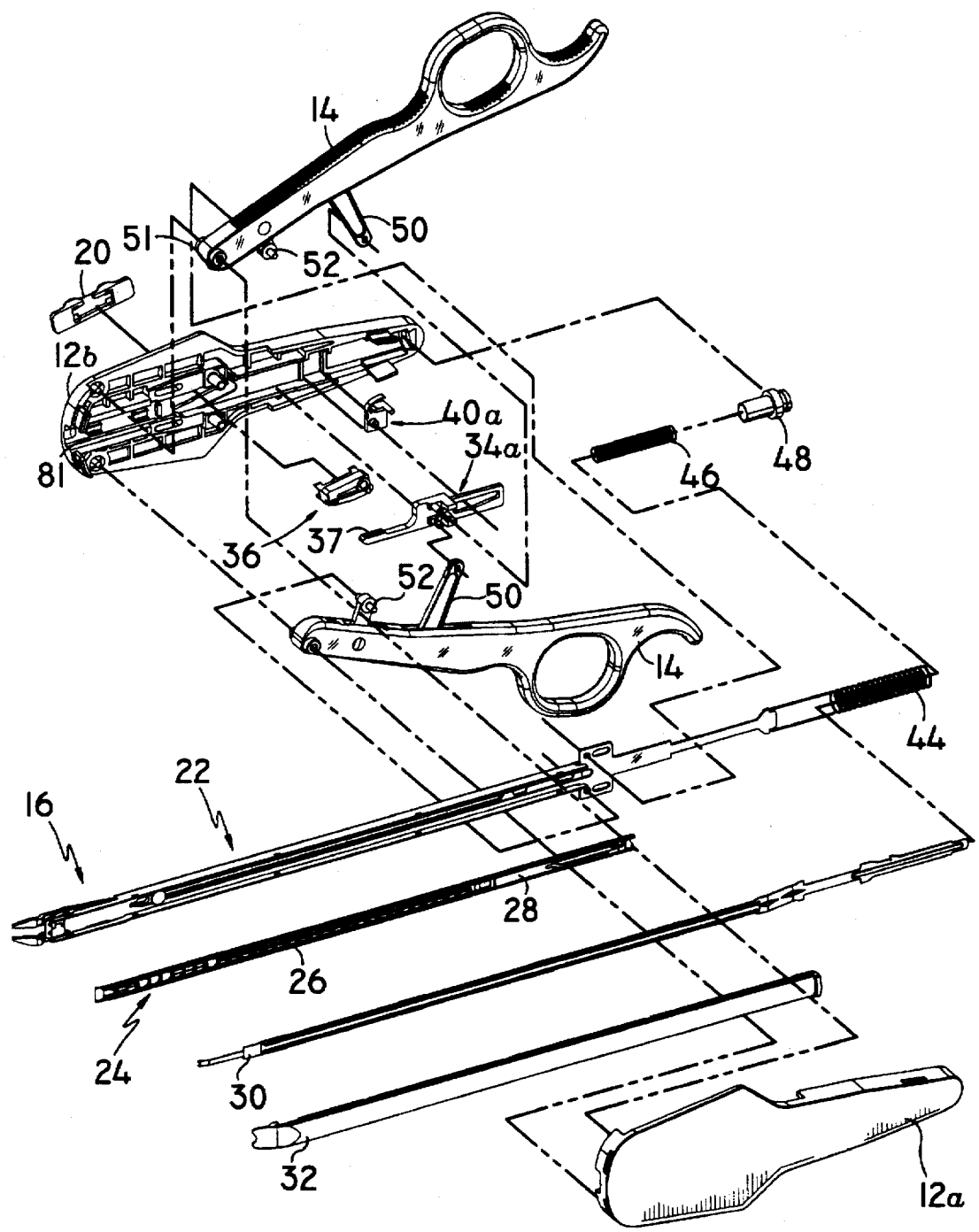
FIG. 7A illustrates an exploded perspective view of an alternate embodiment of the clip applier.

FIG. 7A illustrates an exploded perspective view of clip applier 10, where all the components are substantially the same as those shown in FIG. 7, except for the provision of rack 37 on drive plate 34a. Rack 37 is engaged by pawl 98 of ratchet slide 36 in the manner described with respect to FIG. 7. Ratchet button 20 selectively engages or disengages pawl 98 with rack 37 to selectively engage or disengage the ratchet mechanism.

FIGS. 8–10 illustrate, in an exploded perspective view, the components which make up channel subassembly 22. Channel subassembly 22 includes channel 78, which as described above, is secured against movement to housing 12 through the provision of channel mounting slots 80 which fit over channel mounting posts 81 on the housing half 12b. Slidably positioned within channel 78 is cam plate 73 which functions to open and close the jaw members of jaw subassembly 60. Jaw subassembly 60 includes a pair of jaw members 62 which are connected to each other by bridge portion 64. Jaw subassembly 60 is secured to channel subassembly 22 by jaw anchor rivet 68 which passes through the central slot 91 of cam plate 73, through jaw anchor rivet hole 66 in bridge portion 64, through hole 77 of jaw guard 76, and through rivet hole 79 of channel 78. Cam plate 73 is slidably secured to channel 78 by rivet 68, and is further slidably secured to jaw subassembly 60 through the provision of jaw drive rivets 72 which are positioned in slots 74 and are secured to jaw members 62 at jaw drive rivet holes 70.

Referring to FIG. 9, there is shown the jaw subassembly fully assembled on channel subassembly 22. When assembled, jaw drive rivets 72 are fit in slots 74, thus slidably securing cam plate 73 to the jaw subassembly 60. Anchor rivet 68 slidably secures cam plate 73 to jaw subassembly 60, and further fixedly secures jaw subassembly 60 and jaw guard 76 to channel 78. The cam plate, jaw subassembly and jaw guard arrangement is fit onto channel 78 and under jaw support bridge 82 as shown in FIG. 9.

As best seen in FIGS. 10A–C, cam plate 73 is positioned on jaw subassembly 60 by aligning drive rivets 72 in the mounting keyway 84 of cam slots 74. This permits the larger head of the rivet 72 to pass through the slots 74. Once the cam plate is positioned with respect to drive rivets 72, anchor rivet 68 is positioned as shown through anchor rivet hole 66 in the bridge portion 64 as it passes through the central slot 91 of cam plate 73. Central slot 91 of cam plate 73 terminates at lockout abutment surface 92, whose function will be described hereinbelow.

The construction of jaw subassembly 60 utilizes the natural spring tendency of the material of which jaw subassembly is constructed to maintain the jaws 62 spaced from each other. In this manner, during a closing stroke of the handles, as cam plate 73 moves in the direction of arrow "A" as shown in FIG. 10B, jaw members 62 are cammed towards each other in the direction of arrow "B" as jaw drive rivets 72 ride along surfaces 89 of cam slots 74. Cam slots 74 are designed to provide a constant closing force on the jaw members 62 and consequently on a clip positioned therebetween. To this end, reference is made to FIG. 10C which illustrates the paths of travel of the rivets as cam plate 73 is moved in the direction of arrow "A". Drive rivets 72 travel along first segment 88 and then pass over angled portion 86 of surface 89 and the stroke continues along second segment 90. The angle θ is preferably between about 165° and 175°, and preferably is about 168°. The smooth transition over angled portion 86 permits a constant closing force on the jaw members 62 to efficiently crimp or deform the clip positioned in the jaw members. The angle of segments 88 and 90 also provide for a uniform or constant application force to the handles to effect the deformation of the clip. At the start of the closing stroke, the rate of closure is quick, and therefore the angle of segment 88 is steep with respect to the longitudinal axis. As the rate of closure decreases, as the crimping of the clip proceeds, the angle of the slot, as at segment 90, lessens with respect to the longitudinal axis to keep the force of closure constant during the completion of the closing stroke. That is, the force required to initiate the closing stroke, the force during the closing stroke, and the force required to complete the closing stroke, are substantially the same due to the angle θ between segments 88 and 90.

Referring back to FIGS. 8 and 8A, the proximal end of cam plate 73 includes a flared portion 55 having pivot pin holes 56 provided therein. Pivot pin holes 56 accommodate the pivot pins of links 52 of handle 14 to control movement of the cam plate 73 upon closure of the handles 14. Flared portion 55 also includes frangible portions 57 and lockout slots 58, which will be described in detail below. The proximal end of cam plate 73 includes spring abutment surface 54 which abuts against cam plate spring 44, which fits over spring sleeve 48 as will be described below. Cam plate 73, as described above, also includes rack 38 of the ratchet mechanism.

Referring now to FIGS. 11 and 12, there is illustrated the pusher bar member 30 and the mechanism which controls pusher bar member 30. Pusher bar member 30 terminates at its distal end in nose portion 118, which as shown in FIG. 12, includes nose engaging surface 120 which engages the clips to be fed to the jaw mechanism, and ramped portion 122, whose function will be described below. FIGS. 13A and 13B show the position of nose portion 118 with respect to the distal end of channel cover 32, where nose portion 118 fits within a nose portion groove 128 adjacent the tissue stop 129 of channel cover 32. Channel cover 32 also includes lockout ramp 130, over which pusher bar slot 132 is positioned, and whose function will be described below.

As seen in FIG. 11, drive plate 34 includes pusher bar link post members 94 to which are secured pusher bar links 50 of handles 14. Drive plate 34 also includes driving abutment surface 114 which engages pusher bar drive tab 116, and further includes latch cam slot 106 which accommodates latch post 104 of latch plate 40. Latch post 104 cooperates with cam surface 108 of latch cam slot 106 to release pusher bar 30 to feed a clip to the jaw mechanism as will be described below. Latch plate 40 also includes latching bar 110 which engages latch tab 112 of pusher bar 30 as will be described below.

The proximal end of pusher bar 30 includes spring abutment surface 124 which engages pusher bar spring 46 which is fit in the cavity 126 of spring sleeve 48. Spring 46 biases pusher bar 30 in a distal direction towards the jaw assembly.

Also shown in FIG. 11 is the ratchet mechanism which includes ratchet button 20 to which is secured ratchet slide 36. Ratchet slide 36 includes pawl post 96 upon which pawl 98 is positioned, and pawl tooth 102 is biased into position by pawl spring 100. The function of the ratchet mechanism will be described below.

FIG. 11A illustrates an alternate embodiment of the pusher bar subassembly in which the ratchet mechanism is incorporated into the pusher bar subassembly. FIG. 11A is substantially the same as FIG. 11 except that drive plate 34a includes the rack 37 of the ratchet mechanism, whereby the pawl tooth 102 engages the rack when the ratchet button 20 selectively engages the ratchet mechanism. The function of this mechanism will be described below.

Turning now to FIGS. 14–16, there is illustrated the clip carrier subassembly which includes clip carrier 24 upon which is positioned a series of clips 26 which are urged in the distal direction by clip follower 28. Clip follower 28 includes cam plate lockout 134, having pivot surface 136, ramp surface 137 and blocking surface 138, whose function will be described below. Pivot surface 136 cooperates with pivot surface 154 on clip follower 28 as shown in FIG. 16, and will be described in detail below. Cam plate lockout 134 is positioned in lockout housing 140 at lockout aperture 156.

Figure 17A:
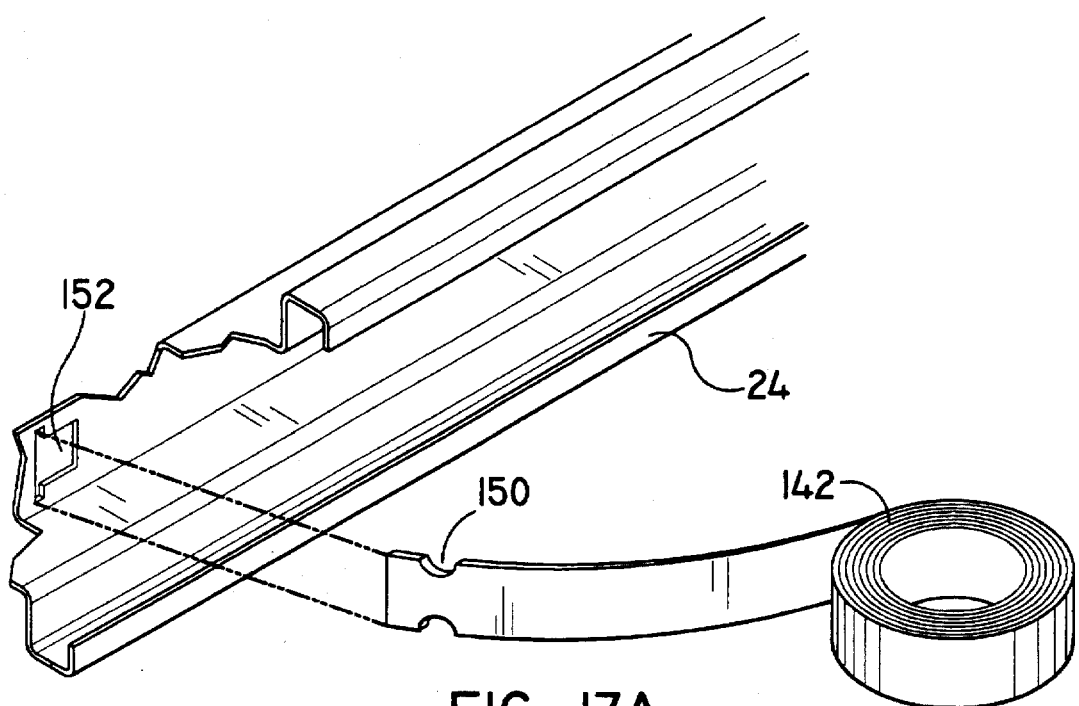
FIGS. 17A and 17B illustrate a perspective view in partial cutaway of the assembly of the clip follower spring to the clip carrier.
Figure 17B:
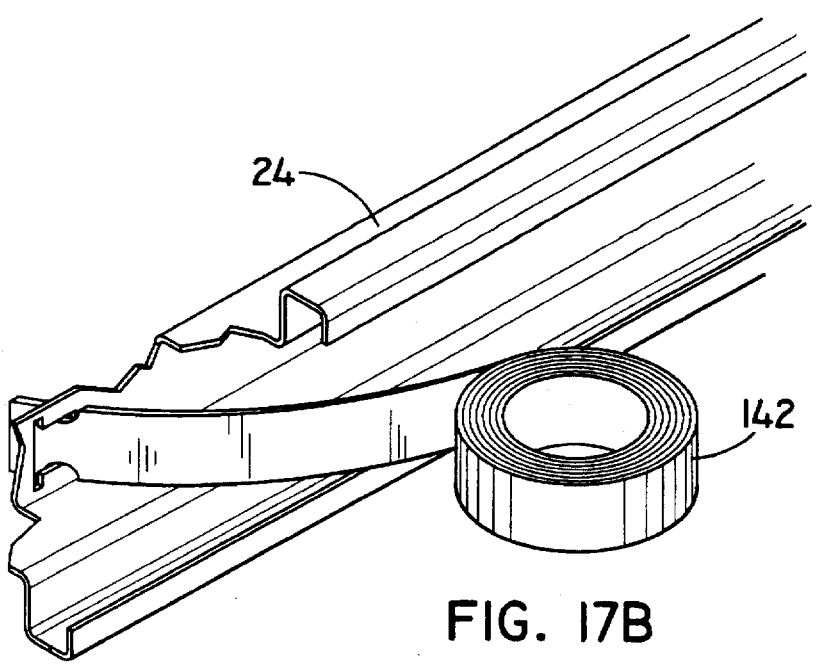

Clip follower 28 also includes clip engaging posts 144, which engage the proximalmost clip in the series of clips to urge the entire series of clips towards the clip exit portion 160 of clip carrier 24. Adjacent clip engaging posts 144 is a lockout aperture 146 which includes blocking wall 148 and ramped surface 158, whose function will be described below. Clip follower 28 is urged in the distal direction by constant force spring 142 which is secured at feed spring tab 150 to feed spring catch 152 on clip carrier 24, as illustrated in FIGS. 17A and 17B. When the series of clips is present on clip carrier 24, constant force spring 142 is unrolled, to provide the biasing force on the series of clips. As the clips are dispensed, spring 142 coils or rolls up on itself, to move clip follower 28 in the distal direction and urge the clips towards the jaw mechanism.

As illustrated in FIGS. 14A and 14B, the series of clips are held in place by the combination of clip holding lance 166 which provides a downward force on the spring, and clip holding lance 168 which provides an upward force on the spring. Clip stop 164 prevents rearward movement of the distalmost clip 26'. As will be described below, clip ramp 162 is at the distal end of clip carrier 24.

Figure 18A:
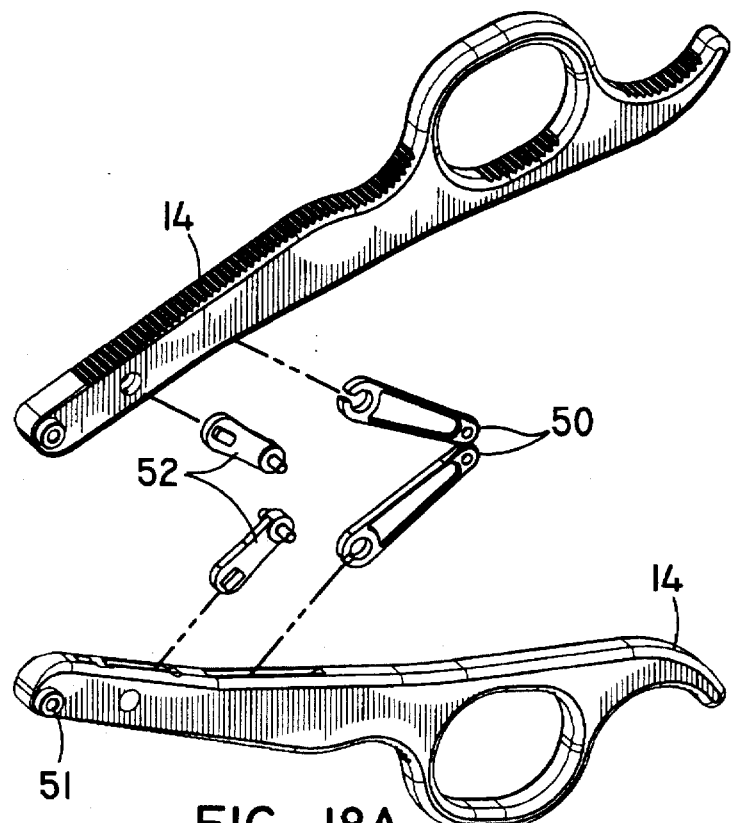
FIGS. 18A–18C illustrate the assembly of the handle members of the clip applier.
Figure 18B:
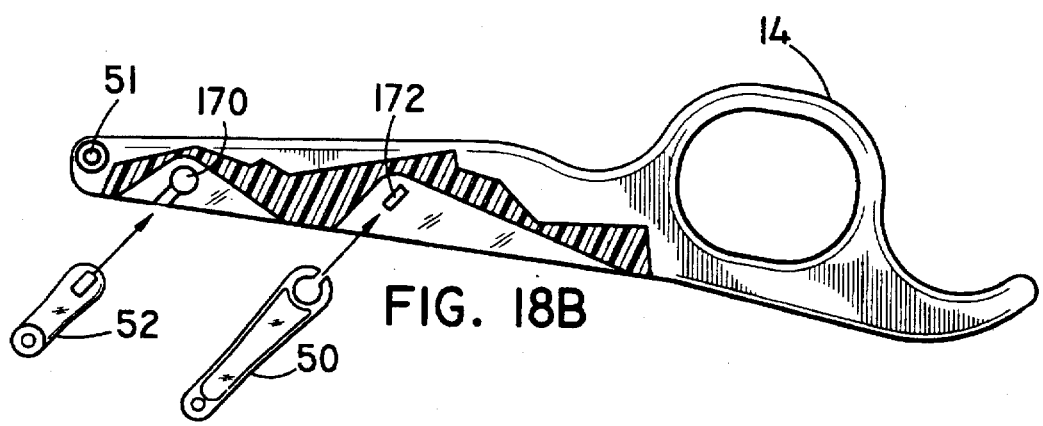
Figure 18C:
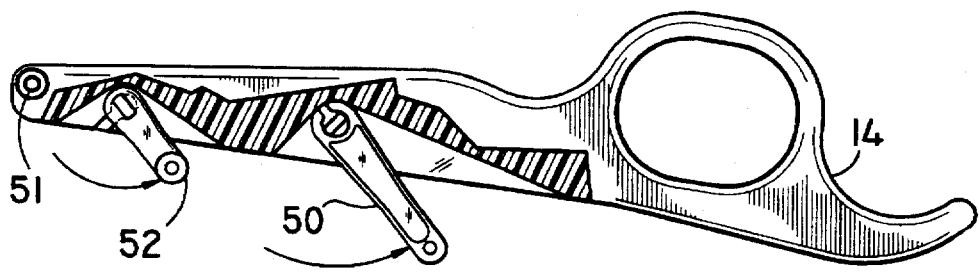

FIGS. 18A–18C illustrate the construction and assembly of handles 14. Links 50 and 52 are secured to the handle 14 at link post 172 and link slot 170, respectively. The post of link 52 slides into slot 170, and the slot of link 50 slides over post 172, as seen in FIG. 18B. The links are then rotated as shown in FIG. 18C to complete the assembly. Handle 14 is secured to housing 12 by handle pivot post 51.

The operation of clip applier 10 will now be described, with particular reference to FIGS. 19–22. Instrument 10 can be packaged with a clip 26 disposed between the jaw members 62 so that the instrument is ready to use immediately or can be packaged with the handles in the closed position, so that as the instrument is removed from the package, the handles move to the open position to feed a clip to the jaws to place the instrument into a "ready" condition. To close a clip, as seen in FIG. 19, handles 14 are moved from the open position to the closed position as shown, which causes a clip 26' to be deformed between the jaw members 62 as shown in FIG. 19A. As the handles close, links 50 and 52 are moved in the proximal direction as shown by the arrows in FIG. 19B. For purposes of this discussion, it will be assumed that the ratchet mechanism is in the engaged state, which is shown in phantom as reference numeral 200 in FIG. 19B. The disengaged state would position ratchet button 20 as shown in phantom at reference numeral 201.

As handles 14 are closed, links 52, whose pivot pins are positioned in pivot pin holes 56 of flared portion 55 of cam plate 73 move the cam plate in the proximal direction against the biasing of spring 44 which is moved to a compressed state by spring abutment surface 54. As cam plate 73 moves rearwardly, pawl tooth 102 of pawl 98 engages the teeth of rack 38 to permit incremental closure of the jaw mechanism. The ratchet mechanism also permits the surgeon to stop during the closing stroke if he so desires without losing the clip from the jaw mechanism. Once handles 14, and consequently cam plate 73 is moved to the position shown in FIGS. 19 and 19B, the jaw members 62 are moved to the position shown in FIG. 19A to deform a clip 26' positioned therebetween. This occurs by moving cam plate 73 in a proximal direction so that drive rivets 72 travel along rivet slots 74 which causes the jaws to be moved towards each other. (See FIG. 10B.) With the ratchet in the on position, a full stroke must be completed for the handles to be moved back to the open position. Since the ratchet is selectable, it may be disengaged during a closing stroke to permit release of a partially closed clip. A partially closed clip may be formed when the ratchet is not engaged during the closing stroke.

As handles 14 are moved to the position shown in FIGS. 19 and 19B, links 50, which are secured to drive plate 34 at pusher bar link post 94 move drive plate 34 in the proximal direction to the position shown in FIG. 19B. As this occurs, the driving abutment surface 114 of drive plate 34 engages drive tab 116 of pusher bar 30 to drive pusher bar 30 in the proximal direction against the biasing of pusher spring 46. As this occurs, latch plate 40, which is biased downwardly by latch spring 42, rides along the edge of pusher bar 30 as pusher bar 30 moves in the proximal direction. Latch locking bar 110 rides on the ramped surface 111 until the ramped surface 111 clears the latch locking bar 110 so that latch locking bar 110 is positioned against pusher bar latch tab 112 as shown in FIG. 19B. Pusher bar 30 is therefore latched into the position shown in FIG. 19B.

Referring to FIG. 19A, it can be seen that the pusher bar 30 has moved proximally so that nose portion 118 is positioned behind the next clip in the series, which is held on clip carrier 24 by clip holding lances 166 and 168 as described above.

Figure 20B:
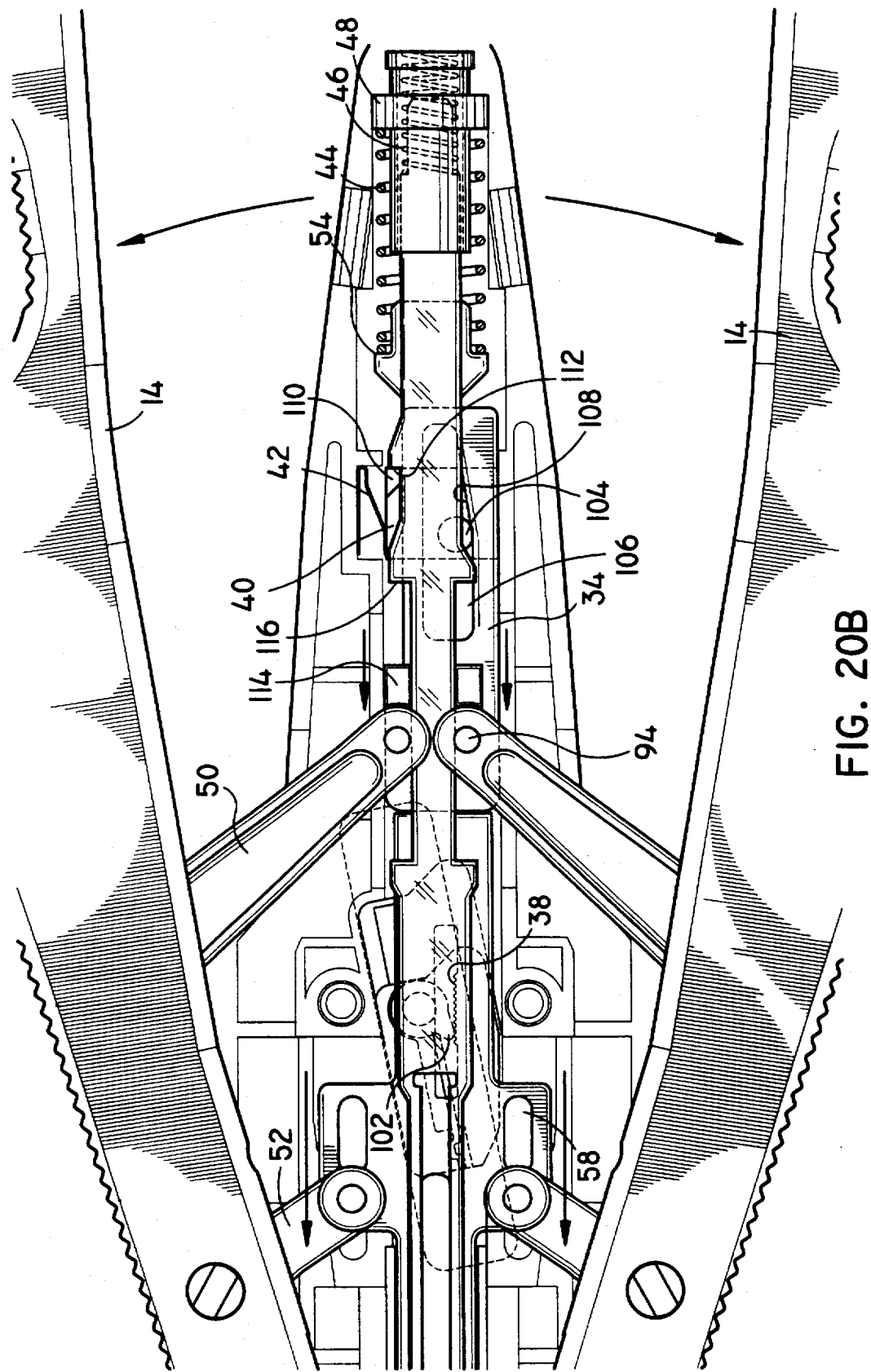
FIG. 20B illustrates a plan view of the housing with the top housing removed showing the position of the components when the handles are in the position as shown in FIG. 20.

As the handles are released, they begin to move from the closed position to the open position under the bias of spring 44, as shown in FIGS. 20, 20A and 20B. As seen in FIGS. 20 and 20B, links 50 and 52 begin to move drive plate 34 and cam plate 73, respectively, in the distal direction towards the jaw mechanism. As can be seen in FIG. 20B, pawl 98, on completion of the closure stroke, completely passes rack 38 and rotates under the biasing of spring 100 to the position shown in FIG. 20B. This permits unimpeded movement of the rack 38 over the pawl tooth 102 to permit the handles to return to an open position. As seen in FIG. 20A, jaw members 62 begin to open as cam plate 73 slides in the distal direction so that rivets 72 travel in the slots 74, forcing the jaw members 62 away from each other. As the handles continue to open, drive plate 34 moves with links 50 in the distal direction as the handles are opened under the influence of spring 44. However, as can be seen in FIGS. 20 and 20B, pusher bar 30 remains latched at pusher bar latch tab 112 as it is engaged by latch locking bar 110 of latch plate 40. Driving abutment surface 114 of drive plate 34 moves away from drive tab 116 of pusher bar 30.

Drive plate 34, as stated above, includes latch cam slot 106 which accommodates latch post 104 of latch plate 40. As drive plate 34 moves in the distal direction, post 104 rides in slot 106 until post 104 engages cam surface 108 of latch cam slot 106. As this occurs, and as will be described with reference to FIGS. 21 and 21B, the ramped surface of cam slot 108 causes post 104 to ride up the ramped surface against the biasing of spring 42. FIG. 20A shows the nose portion 118 of pusher bar 30 in position behind the distalmost clip 26' of the series of clips ready to be fed into the jaw members 62.

Figures 21, 21A:
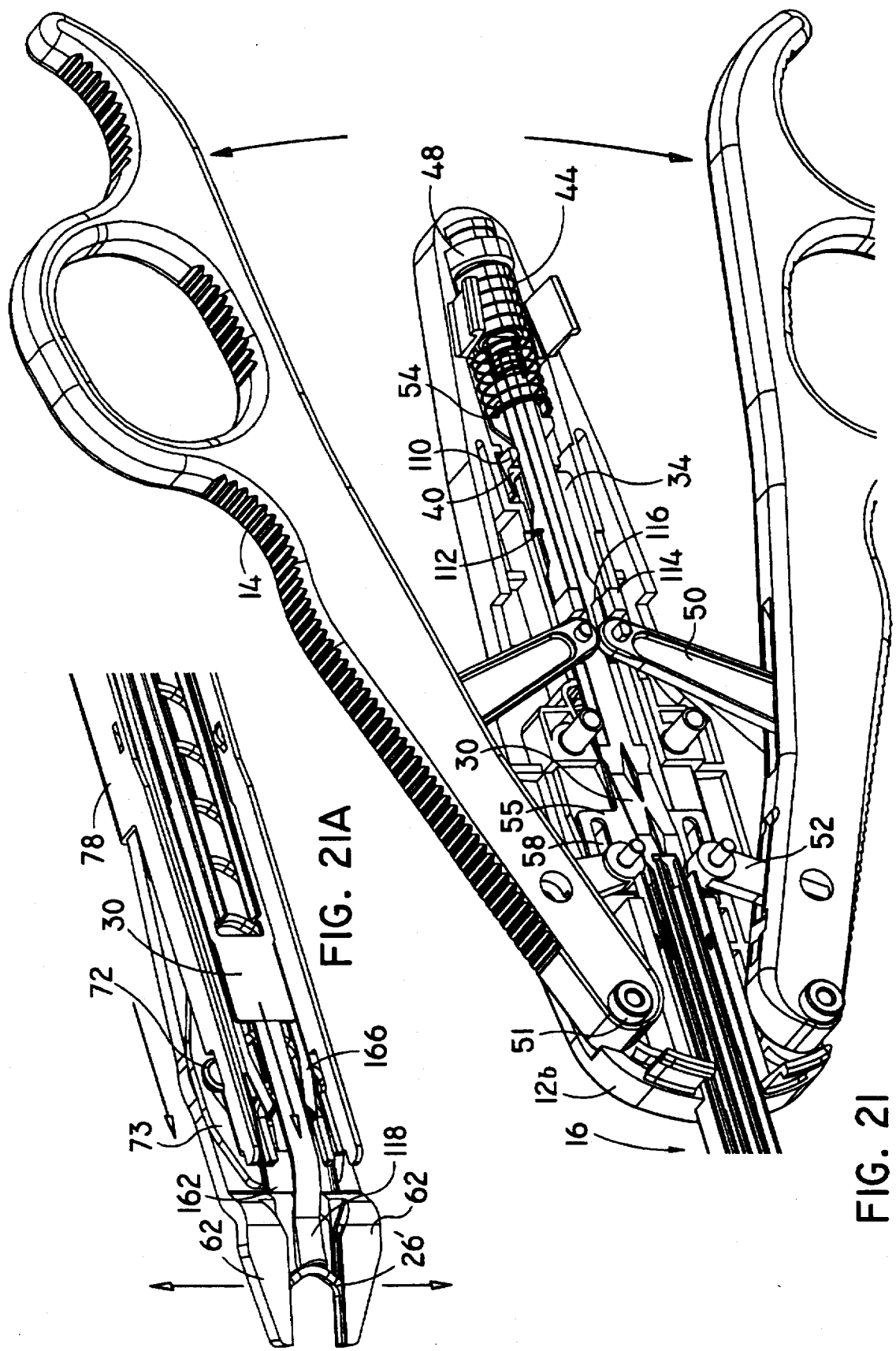
FIG. 21 illustrates a perspective view with the top housing removed showing the position of the components when the handles are in the fully opened position.
FIG. 21A illustrates a perspective view of the distal end of the instrument with the channel cover removed showing the position of the components when the handles are in the position shown in FIG. 21.
Figure 21B:
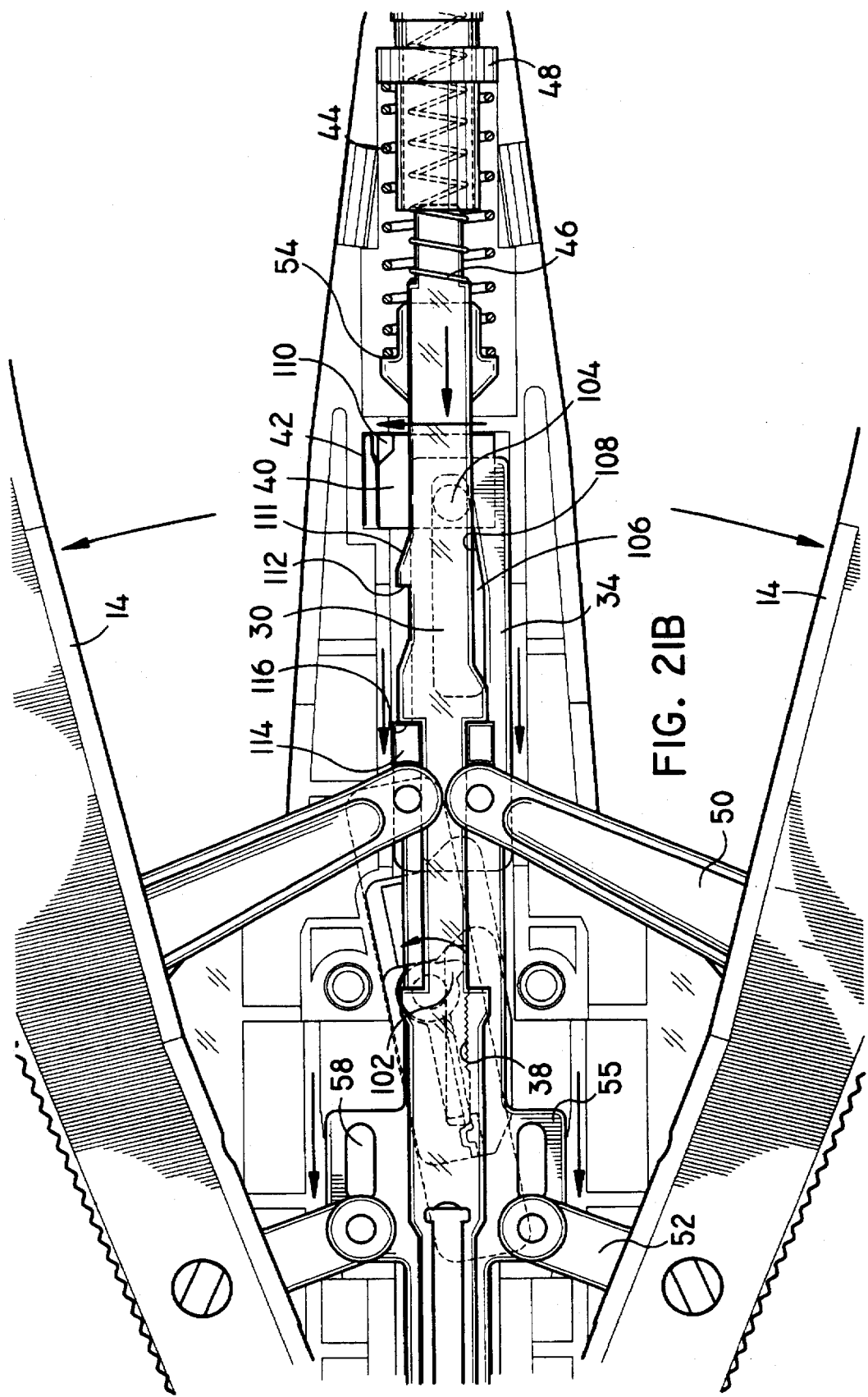
FIG. 21B illustrates a plan view with the top housing removed showing the position of the components when the handles are in the fully opened position of FIG. 21.

Referring now to FIGS. 21, 21A and 21B, as the handles fully open, post 104 has moved along the ramped surface of cam surface 108 to lift latch locking bar 110 over pusher bar latch tab 112. Due to the biasing of spring 46, pusher bar 30 moves in the distal direction until pusher bar drive tab 116 engages driving abutment surface 114 of drive plate 34 as shown in FIG. 21B. As seen in FIG. 21A, at this time cam plate 73 has returned to the at rest position where drive rivet 72 is in the proximalmost end of drive slots 74, thus opening the jaw members 62 fully to accept the clip 26'. Once latch locking bar 110 has cleared pusher bar latch tab 112, pusher bar 30 is moved under the bias of spring 46 in the distal direction so that nose portion 118 slides the distalmost clip 26' into position between the jaws. At this point, the instrument is ready to apply another clip and is in the "ready" position. As also seen in FIG. 21B, the pawl 98 has rotated to its "ready" position to engage the rack 38 upon the closing stroke of the handles 14.

Figure 22C:
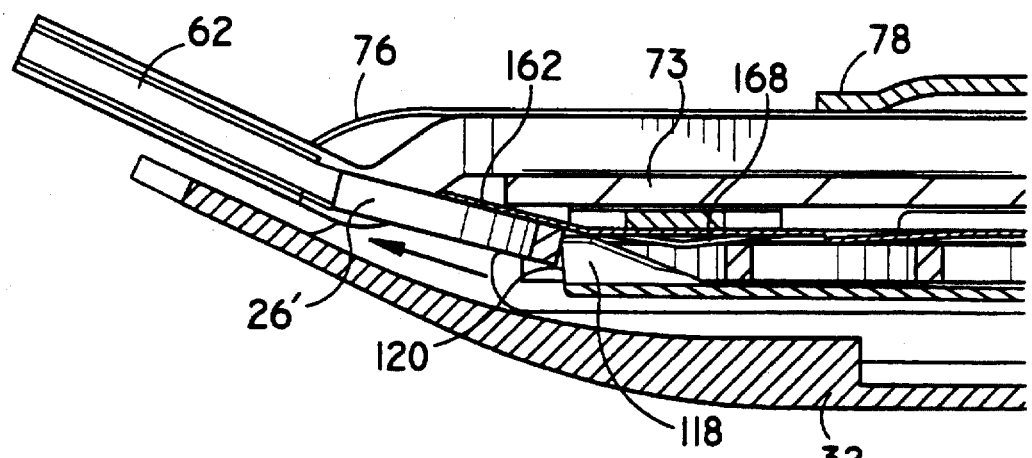
FIGS. 22C–22E illustrate a side cross-sectional view of the clip feeding process.
Figure 22D:
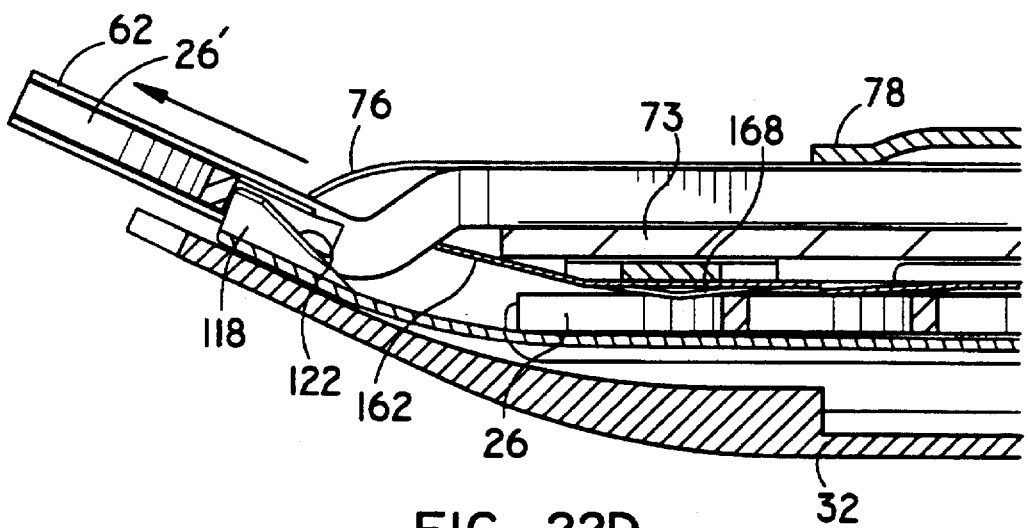
Figure 22E:
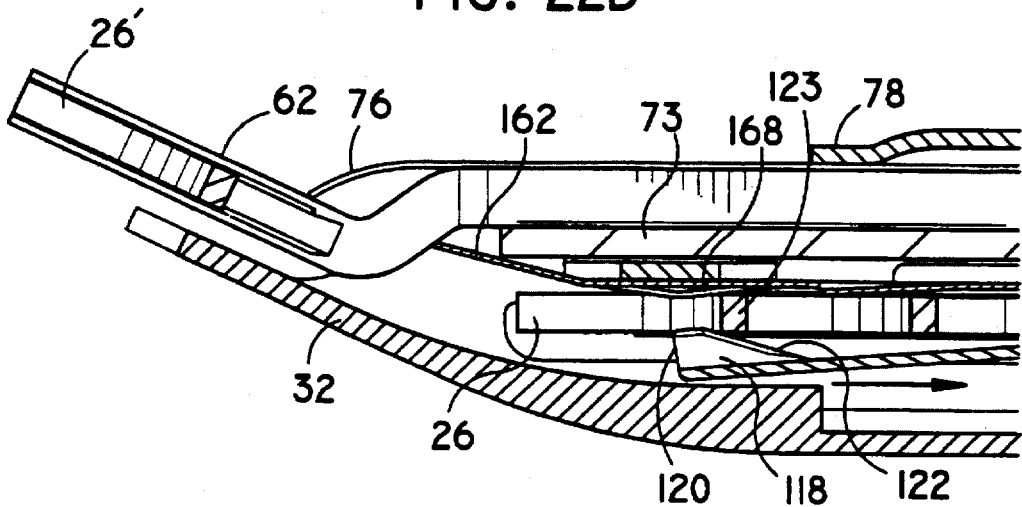

FIGS. 22 and 22A–22E illustrate a cross-sectional view of the clip loading process at the distal end of the instrument. FIG. 22 shows the instrument in the position shown as described above with reference to FIGS. 19, 19A and 19B in which the jaws are closed and the pusher bar 30 has its nose portion 118 positioned behind the distalmost clip 26' ready to feed the clip to the jaws. FIG. 22A shows the "ready" position in detail where lances 166 and 168 hold the distalmost clip 26' in position with the nose portion 118 of pusher bar 30 ready to deliver the clip to the jaw members 62. FIG. 22B shows the beginning of the release stroke of the pusher bar 30 corresponding to that shown above with respect to FIGS. 21, 21A and 21B. As seen in FIG. 22B, as the nose portion 118 begins to move in a distal direction, the clip 26' is pushed over the center portion of lance 168 so that it begins to tilt in an upward direction along clip ramp 162 of clip carrier 24. As the nose portion 118 engages the clip at nose engaging portion 120, the clip enters the anvil surface of the jaw members 62 as it rides along clip ramp 162 as seen in FIG. 22C. FIG. 22D shows the pusher bar 30 extending its nose portion all the way into the jaws to properly seat clip 26' between the jaw members 62. As this is occurring, clip follower 28 urges the entire series of clips in a distal direction so that the next clip in the series is positioned on clip holding lances 166 and 168. This position of the nose portion 118 of pusher bar 30 corresponds to that shown in FIGS. 21, 21A and 21B. As the next closing stroke of the handles begins, the pusher bar 30 is moved in the proximal direction, such as shown in FIG. 19B, and the nose portion 118 is retracted to the position behind the next distalmost clip in the series of clips, as shown in FIG. 22E. The ramped portion 122 of nose 118 permits nose 118 to ride over the bight portion 123 of the next clip as it is moved out of the way so that it may align itself behind the next distalmost clip 26. Operation of the instrument is then repeated as indicated above.

Figure 24B:
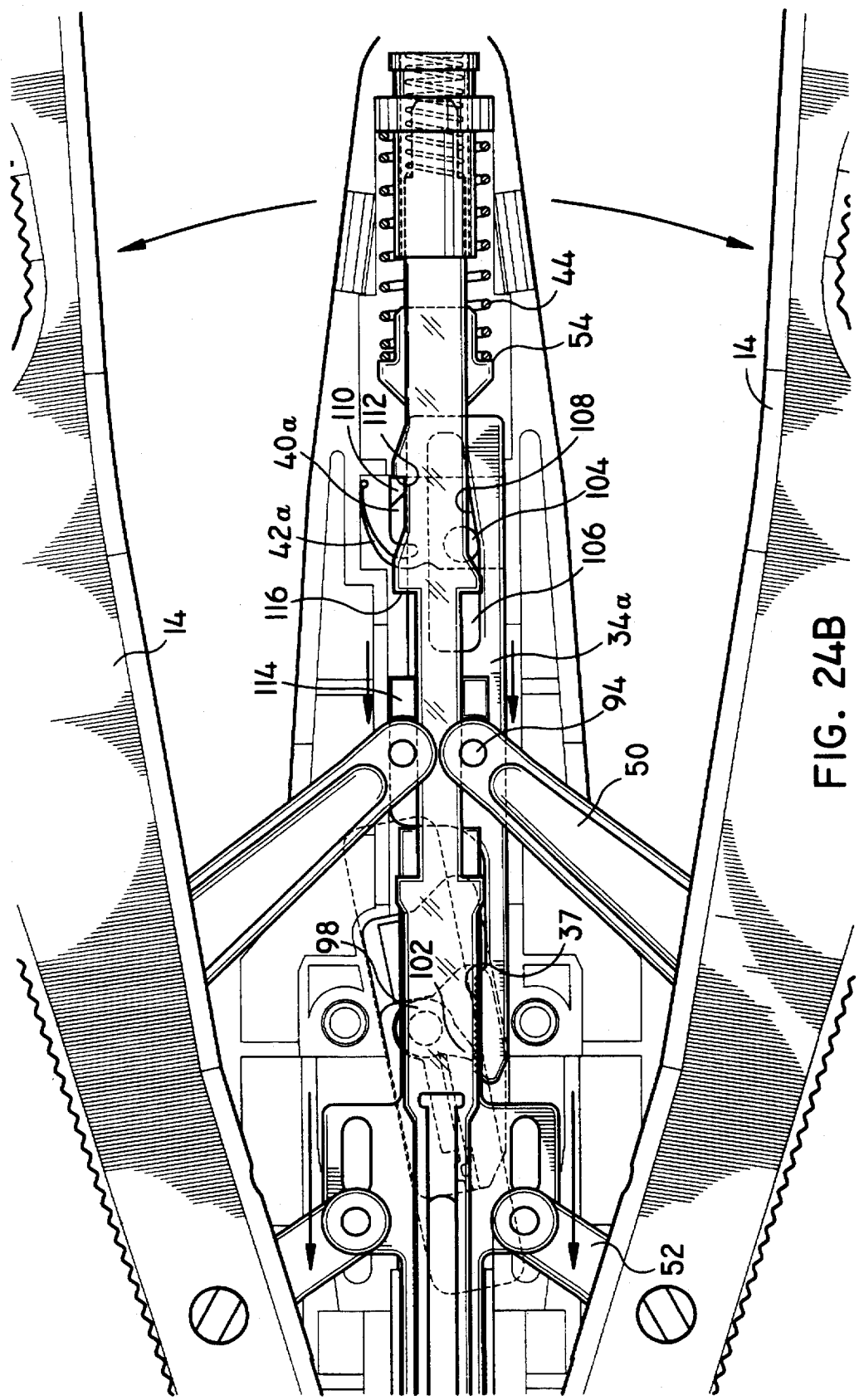
Figures 25, 25A:
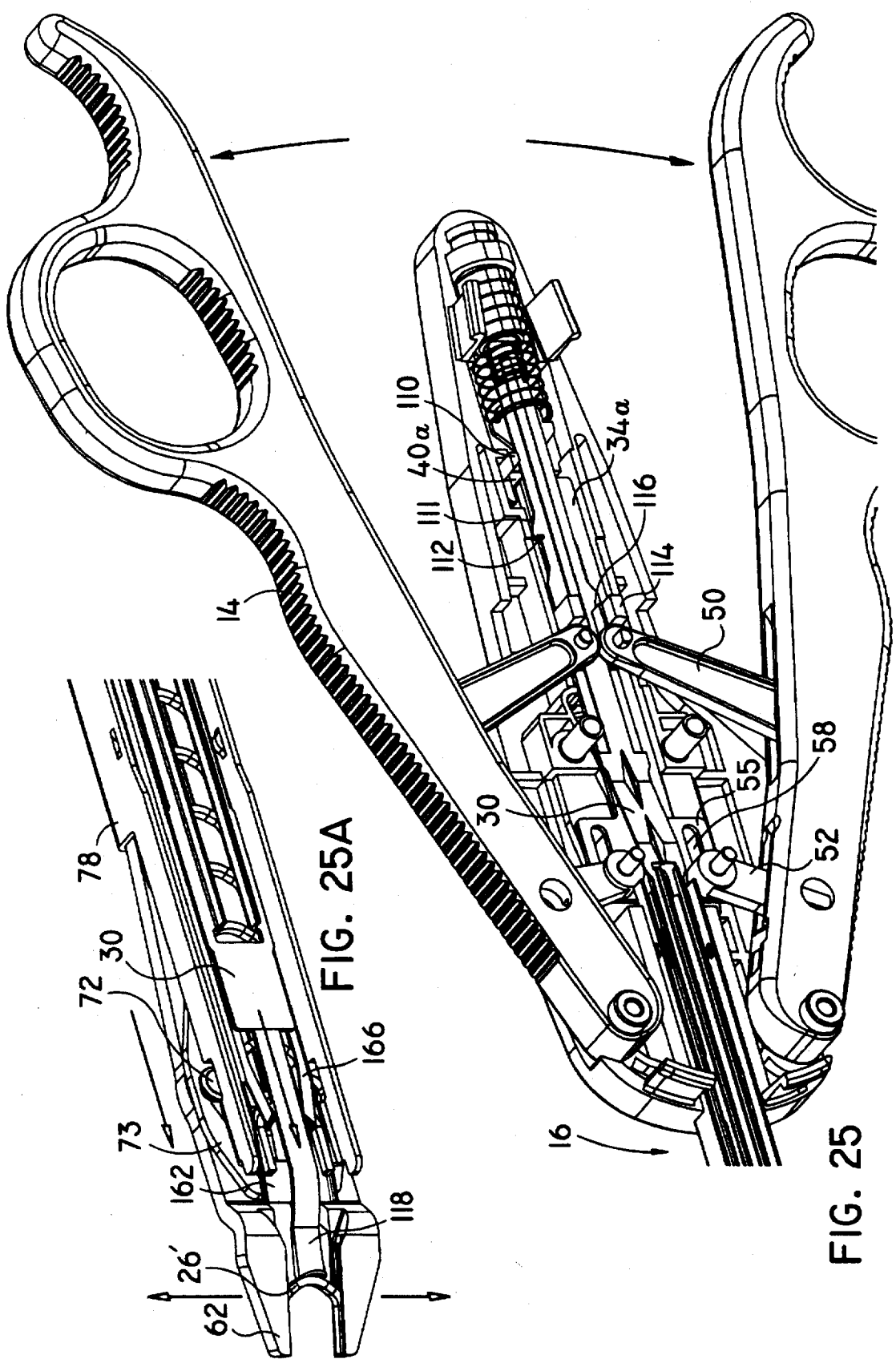
Figure 25B:
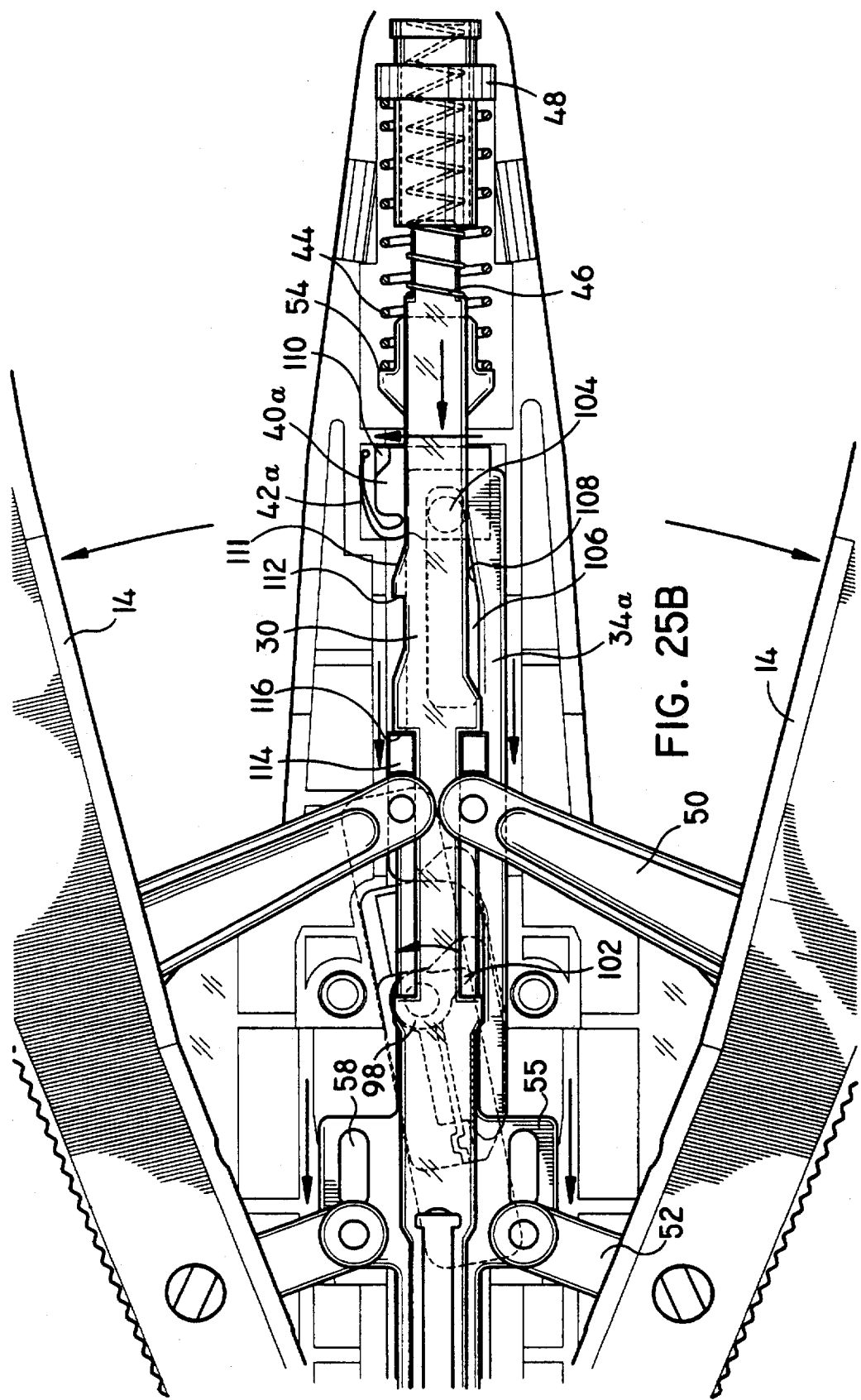

FIGS. 23–25 show the alternate embodiment of the ratchet mechanism, in which the rack 37 is integral with the drive plate 34a. In addition, there is illustrated the alternate embodiment of the latch plate 40a in which the latch spring 42a is integral with the latch plate 40a. Operation of the instrument is identical to that as described above with respect to FIGS. 19–21.

Operation of the novel lockout mechanism of clip applier 10 will now be described with respect to FIGS. 26 and 26A. After the application of the last clip in the series of clips, the lockout mechanism operates to block movement of the cam plate 73 as well as movement of the pusher bar 30, and further provides a mechanism for disabling the instrument to render it inoperative. When the last clip is loaded to a position between the jaw members 62, (such as shown in FIGS. 21A and 22D but without any clips on clip carrier 24 except for the clip 26' between jaw members 62), pusher bar 30 is fully extended so that nose portion 118 is in between the jaw members 62 with its nose engaging surface 120 abutting the bight portion of the clip 26'. As the handles begin to close to form the last clip, (as described above with respect to FIGS. 19, 19A and 19B), the pusher bar 30 begins to move in the proximal direction along with cam plate 73. When the handles are fully closed, cam plate 73 is in its proximal most position, as is pusher bar 30. When this occurs, with reference to FIGS. 26 and 10, the solid portion 93 of cam plate 73, adjacent lockout abutment surface 92, prevents the upward movement of lockout 134 as its ramped surface 137 engages lockout ramp 130 and pivoting surface 136 pivots about pivot surface 154. However, since pusher bar 30 is in its proximal most position, nose portion 118 returns to the position shown in FIG. 26, where ramped portion 122 of nose portion 118 rides over ramped portion 158 of clip follower 28. As the nose portion 118 clears the ramped portion 158 of clip follower 28, nose portion 118 drops into lockout aperture 146 of clip follower 28. Movement of pusher bar 30 in the distal direction is now prevented by the engagement of nose engaging portion 120 with blocking wall 148 of the lockout aperture 146 as shown in FIG. 26A.

As the handles are released, nose portion 118 remains within lockout aperture 146 as shown in FIGS. 26 and 26A, while cam plate 73 begins to return to its at rest position as it moves distally to open the jaw members 62. As cam plate 73 returns to the position shown in FIG. 21A, the solid portion 93 of cam plate 73 passes over cam plate lockout 134 until lockout 134 is pivoted into slot 91 of cam plate 73 due to the biasing force of spring 142 and the lockout ramp 130 which cams against the ramped surface 137 of cam plate lockout 134. As cam plate lockout 134 pivots to the position shown in FIG. 26, cam plate lockout 134 pivots through the central slot 132 of pusher bar 30 until blocking surface 138 is adjacent to and engages lockout abutment surface 92 of cam plate 73 as shown in FIG. 26. Cam plate lockout 134 also pivots upwardly through lockout aperture 156 of clip follower 28.

When the lockout mechanism is in place as shown in FIGS. 26 and 26A, any attempt at closing the handles results in cam plate 73 attempting to move in a proximal direction, but is prevented from doing so by the engagement between blocking surface 138 and abutment surface 92. This effectively prevents the jaw members 62 from closing. At the same time, pusher bar 30 is prevented from moving in a distal direction by the engagement between nose engaging surface 120 of nose portion 118 with blocking wall 148 of lockout aperture 146. With reference to FIG. 8, in the event that a user applies excessive force to the handles in an attempt to close them and override the lockout mechanism shown in FIGS. 26 and 26A, frangible portion 57 of flared portion 55 of cam plate 73 will rupture, thereby causing the pivot pin of link 52 to move freely between pivot pin hole 56 and lockout slot 58, rendering the handle mechanism inoperable. Alternately, it is contemplated that the pivot pin of link 52 may shear to provide the same result, and furthermore a keyway system is also contemplated in which the pivot pin will be redirected to a lockout slot without the need for a frangible portion.

While the clip applier has been particularly shown and described with reference to the preferred embodiments, it will be understood by those skilled in the art that various modifications and changes in form and detail may be made therein without departing from the scope and spirit of the novel aspects of the above-described clip applier. Accordingly, modifications such as those suggested above, but not limited thereto, are to be considered within the scope of what is considered to be the invention.

What is claimed:

1. A surgical clip applier comprising:
   a housing;
   a pair of handles pivotably connected to opposite sides of said housing;
   an elongate body portion fixedly secured to and extending from said housing and carrying a plurality of clips;
   a jaw assembly fixedly secured to and extending from an end of said body portion opposite said housing, said jaw assembly adapted to accommodate a clip therein; and
   a cam plate slidably positioned in said body portion, said cam plate being operatively connected at a first end to at least one of said handles and at a second end to said jaw assembly, such that moving said handles from an open position to a closed position causes a sliding movement of said cam plate with respect to said body portion and said jaw assembly to effect closure of a clip in said jaw assembly.

2. A surgical clip applier according to claim 1, wherein said jaw assembly comprises a pair of jaw members each having a clip engaging surface at a distal end and a bridging portion at proximal end, said jaw members being connected at said bridging portion, and said jaw assembly being secured to said body portion at said bridging portion.

3. A surgical clip applier according to claim 2, wherein said cam plate is operatively connected to each jaw member by a post member which is disposed in a cam slot, such that sliding movement of said cam plate causes movement of said post members through said cam slots to simultaneously move said jaw members towards and away from each other.

4. A surgical clip applier according to claim 3, wherein said cam plate is provided with a pair of cam slots which accommodate a post member extending from each jaw member, such that sliding movement of said cam plate slides said slots over said post members to simultaneously move said jaw members towards and away from each other.

5. A surgical clip applier according to claim 2, wherein said cam plate is provided with a pair of cam slots which accommodate a post member extending from each jaw member, such that sliding movement of said cam plate slides said post members through said cam slots to simultaneously move said jaw members towards and away from each other.

6. A surgical clip applier according to claim 4, wherein said cam slots each define a path of travel for its respective post member having first and second segments which are offset by an angle, such that said paths of travel moves said post members towards a longitudinal axis of said body portion and said cam plate to close said jaw members.

7. A surgical clip applier according to claim 6, wherein said angle between said first and second segments provides a constant closing force on said clip in said jaw assembly.

8. A surgical clip applier according to claim 6, wherein said angle between said segments is in the range of about 165° to 175°.

9. A surgical clip applier according to claim 5, wherein said plurality of clips are arranged serially in end to end relation for serial delivery to said jaw assembly.

10. A surgical clip applier according to claim 9, further comprising a clip pusher member slidably positioned in said body portion, said pusher member being operatively connected to at least one of said handles at a first end and having a nose portion terminating adjacent said jaw members at a second end, said pusher member being moved towards said housing as said handles are closed to move said nose portion behind a distalmost clip in said series of clips, said pusher member being moved towards said jaw assembly as said handles are opened to move said distalmost clip between said jaw members.

11. A surgical clip applier according to claim 1, further comprising a ratchet mechanism operatively associated with said cam plate to permit incremental closure of said jaw assembly, said ratchet mechanism being selectively engagable and disengagable.

12. A surgical clip applier according to claim 11, wherein the selectability of said ratchet mechanism permits partial closure of a clip positioned in said jaw assembly.

13. In a surgical clip applier having a housing, a pair of handles pivotably connected to the housing, a channel assembly fixed to and extending from the housing, a series of clips arranged serially in end to end relation and carried by the channel assembly, a pair of jaw members secured to and extending from an end of the channel assembly opposite the housing, a clip follower for urging the series of clips towards the jaw members, a clip pusher member slidably disposed in the channel assembly for advancing a distalmost clip from the series of clips to a position between the jaw members in response to movement of the handles, and a jaw closure camming mechanism to effect closure of the jaw members to deform a clip positioned therebetween in response to movement of the handles, the camming mechanism including a cam plate slidably disposed intermediate the pair of handles and the jaw member, the improvement which comprises:

a lockout mechanism for rendering the clip applier inoperable upon deforming a last clip of the series of clips, the lockout mechanism including a first blocking member associated with the clip follower for engagement with the cam plate to prevent movement of the cam plate, and at least one frangible member to disengage the cam plate from the handles upon closure of the handles when the first blocking member is engaged with the cam plate.

14. The clip applier of claim 13, further comprising a second blocking means for engagement with the clip pusher member to prevent movement of the clip pusher member upon deforming a last clip in the series of clips.

15. The clip applier of claim 14, wherein the first blocking member and the second blocking means are operatively associated with the clip follower.

16. The clip applier of claim 15, wherein the first blocking member is pivotable into engagement with a portion of the cam plate to prevent sliding movement of the cam plate which prevents closing of the jaw members, and the second blocking means defines wall portions surrounding an aperture in the clip follower, the clip pusher member being pivotable into the aperture and into engagement with at least one of the wall portions to prevent movement of the clip pusher member.

17. The clip applier of claim 13, wherein the handles are connected to the cam plate by pivot pins positioned in holes in the cam plate, and wherein the frangible members are defined by a portion of the cam plate adjacent to and between the pivot pin holes and an aperture in said cam plate, the frangible members being ruptured upon application of a predetermined force on the handles subsequent to the first blocking member being engaged with the cam plate.

18. The clip applier of claim 13, wherein the handles are connected to the cam plate by pivot pins, and wherein the frangible members are defined by the pivot pins which rupture upon application of a predetermined force on the handles subsequent to the first blocking member being engaged with the cam plate.

19. A surgical clip applier comprising:

a housing;

a pair of handles pivotably connected to opposite sides of the housing;

a channel assembly fixedly secured to and extending from an end of the housing and carrying a series of clips in end to end relation;

a jaw assembly having a pair of opposed jaw members fixedly secured to and extending from an end of the channel assembly opposite the housing, the jaw members having a clip positioned therebetween;

a clip pusher member slidably disposed in the channel assembly and being operatively connected at one end to at least one of the handles, the pusher member having a nose portion at a second end for engaging a distalmost clip in the series of clips and being operable to move the distalmost clip to a position between the jaw members; and a cam plate slidably disposed in the channel assembly and being operatively connected at one end to at least one of the handles, the cam plate being operatively connected at a second end to said jaw assembly;

wherein movement of the handles from an open position to a closed position causes the cam plate and the pusher member to simultaneously move in a proximal direction towards the housing, such that the cam plate moves towards the housing to effect closure of the jaw members to deform the clip, and the pusher member moves towards the housing to position the nose portion behind the distalmost clip in the series of clips, and wherein movement of the handles from the closed position to the open position causes the cam plate to move towards the jaw assembly to effect opening of the jaw members to release the deformed clip, and causes the pusher member to move towards jaw assembly to advance the distalmost clip in the series of clips to a position between the jaw members.

20. A surgical clip applier according to claim 19, wherein the housing, the channel assembly and the jaw assembly are stationary with respect to the cam plate and clip pusher member during opening and closing movement of the handles.

21. A surgical clip applier according to claim 19, wherein movement of the handles from the closed position to the open position causes movement of the pusher member and cam plate towards the jaw assembly, such that movement of the pusher member is delayed from and subsequent to movement of the cam plate towards the jaw assembly to allow the jaw members to open to accommodate a clip therebetween.

* * * * *